US012133707B2

(12) United States Patent
Zhang et al.

(10) Patent No.: US 12,133,707 B2
(45) Date of Patent: Nov. 5, 2024

(54) EVALUATION OF CALIBRATION FOR SURGICAL TOOL

(71) Applicant: Verb Surgical Inc., Santa Clara, CA (US)

(72) Inventors: Xiaobin Zhang, Santa Clara, CA (US); Alireza Hariri, Santa Clara, CA (US)

(73) Assignee: Verb Surgical Inc., Santa Clara, CA (US)

( * ) Notice: Subject to any disclaimer, the term of this patent is extended or adjusted under 35 U.S.C. 154(b) by 533 days.

(21) Appl. No.: 17/397,248

(22) Filed: Aug. 9, 2021

(65) Prior Publication Data

US 2023/0046044 A1 Feb. 16, 2023

(51) Int. Cl.
*A61B 34/00* (2016.01)
*A61B 34/30* (2016.01)
*A61B 34/35* (2016.01)
*B25J 9/10* (2006.01)
*B25J 9/16* (2006.01)

(52) U.S. Cl.
CPC ............ *A61B 34/71* (2016.02); *A61B 34/35* (2016.02); *B25J 9/1045* (2013.01); *B25J 9/1641* (2013.01); *B25J 9/1692* (2013.01); *A61B 2034/305* (2016.02)

(58) Field of Classification Search
CPC ... A61B 34/71; A61B 34/35; A61B 2034/305; B25J 9/1045; B25J 9/1641; B25J 9/1692
See application file for complete search history.

(56) References Cited

U.S. PATENT DOCUMENTS

| | | | |
|---|---|---|---|
| 9,002,518 B2 * | 4/2015 | Manzo | A61B 90/98 901/19 |
| 9,649,174 B2 * | 5/2017 | Swarup | A61B 34/71 |
| 10,166,082 B1 | 1/2019 | Hariri et al. | |
| 10,595,836 B2 * | 3/2020 | Smaby | A61B 17/00 |
| 10,595,946 B2 * | 3/2020 | Nixon | G16Z 99/00 |
| 10,661,453 B2 * | 5/2020 | Koenig | B25J 13/02 |
| 10,888,370 B2 * | 1/2021 | Shelton, IV | A61B 18/1445 |
| 11,192,243 B2 * | 12/2021 | Nilsson | B25J 9/1653 |
| 11,547,511 B2 * | 1/2023 | Asadian | A61B 34/25 |
| 2003/0036748 A1 | 2/2003 | Cooper et al. | |
| 2008/0046122 A1 | 2/2008 | Manzo et al. | |
| 2008/0154246 A1 | 6/2008 | Nowlin et al. | |
| 2009/0088775 A1 | 4/2009 | Swarup et al. | |
| 2010/0087835 A1 | 4/2010 | Blumenkranz et al. | |
| 2015/0150635 A1 | 6/2015 | Kilroy et al. | |
| 2016/0303743 A1 | 10/2016 | Rockrohr | |

(Continued)

FOREIGN PATENT DOCUMENTS

CN 110248616 A * 9/2019 ....... A61B 17/00234

*Primary Examiner* — Octavia Hollington
(74) *Attorney, Agent, or Firm* — Lempia Summerfield Katz LLC

(57) ABSTRACT

The disclosure relate to systems and methods for a surgical tool or a surgical robotic system. An example computer-implemented method for evaluating calibrations of a surgical tool includes fixating a joint of the surgical tool at a first angle, the joint being driven by an actuator, measuring an actuator position corresponding to the first angle, accessing a calibrated offset corresponding to the first angle, determining an expected joint angle based on the measured actuator position and the calibrated offset, and reporting a first difference between the expected joint angle and the first angle.

20 Claims, 12 Drawing Sheets

(56) References Cited

U.S. PATENT DOCUMENTS

| | | | |
|---|---|---|---|
| 2020/0054401 A1* | 2/2020 | Yu | ............................ B25J 9/1633 |
| 2021/0282876 A1* | 9/2021 | Ergueta Tejerina | ............................ A61B 17/3201 |
| 2023/0112334 A1* | 4/2023 | Zhang | ..................... A61B 34/35 606/1 |

* cited by examiner

EVALUATION OF CALIBRATION FOR SURGICAL TOOL

FIELD

This disclosure relates to engagement, calibration, and/or additional control of a surgical robotic tool with one or more actuators.

BACKGROUND

Surgical robotic systems give an operator or user, such as an operating surgeon, the ability to perform one or more actions of a surgical procedure. In the surgical robotic system, a surgical tool or instrument, such as an endoscope, clamps, cutting tools, spreaders, needles, energy emitters, etc., is mechanically coupled to a robot joint of a surgical robotic arm, so that movement or actuation of the robot joint directly causes a rotation, pivoting, or linear movement of a part of the tool. Once the tool is attached to (e.g., in contact with) a tool driver in the arm, operator commands may cause movements and activate functions of the attached tool.

Due to the varied nature of surgical procedures, different surgical tools or instruments may be selectively attached to the same arm of a surgical robotic system before and during a surgical procedure. In order to avoid equipment malfunctions during a surgical procedure, it is important that the surgical tool or instrument not only be attached to but also mechanically engaged to the robot joint of the surgical robotic arm. That is, mechanisms in the surgical tool that impart motion or enable the activation of instrument features should be mechanically engaged to the actuators that are in the tool driver of the arm of the surgical robotic system before the surgical tool is in use during the surgical procedure.

Through complex processes such as engagement, homing, and calibration. A relationship may be established between the tool driver and the surgical tool. However, challenges remain in evaluation of the accuracy of this established relationship. For example, in situations in which the surgical tool has been calibrated, merely repeating the calibration will only show how repeatable the calibration process is. However, such a test result cannot answer whether the calibration result is accurate or not. It is possible that a bad calibration process can generate consistently wrong results.

SUMMARY

Disclosed herein is a robotically-assisted surgical electromechanical system designed for surgeons to perform minimally-invasive surgery. A suite of compatible tools can be attached/detached from an instrument driver mounted to the distal end of a robotic arm, enabling the surgeon to perform various surgical tasks. The instrument drivers can provide intracorporeal access to the surgical site, mechanical actuation of compatible tools through a sterile interface, and communication with compatible tools through a sterile interface and user touchpoints.

One example system for testing a calibration of a tool driver includes a surgical tool, a lock and one or more processors. The surgical tool is connected to and driven by at least one motor of the tool driver. The lock is configured to hold the surgical tool in a predetermined tool position. The one or more processors are configured to identify a lock identifier for a lock associated with at least one joint of the surgical tool, provide a motor command for at least one motor associated with the at least one joint of the surgical tool, determine a motor position for the motor, and store, in a memory, the determined motor position in association with the lock identifier.

One example method for operation of testing a calibration of an end effector, includes receiving a lock identifier for a lock associated with at least one joint of the end effector, providing a motor command for a motor associated with the at least one joint of the end effector and a predetermined tension to a cable for the at least one joint of the end effector, measuring a motor position for the motor, and storing, in a memory, the measured motor position in association with the lock identifier.

One example apparatus for evaluation of a calibration procedure for a surgical tool includes a memory storing expected values for a plurality of motors coupled to the surgical tool and the one or more processors further configured to identify at least one lock identifier for a lock associated with at least one joint of the surgical tool, provide a motor command for at least one motor associated with the at least one joint of the surgical tool, determine a motor position for the motor, access data for an expected motor position from the memory, and compare the measured position to the expected motor position.

DETAILED DESCRIPTION

Figure 1:
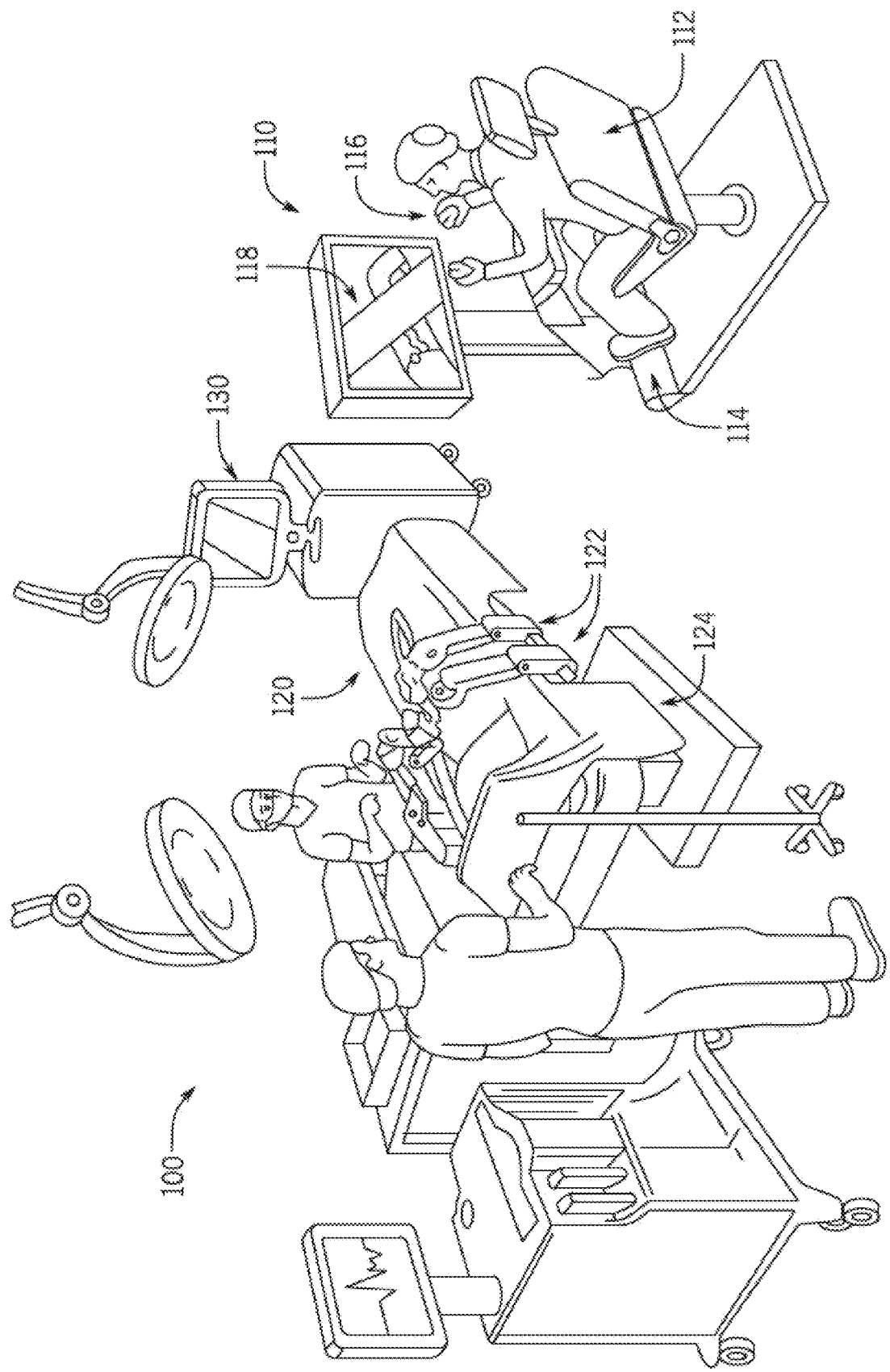
FIG. 1 illustrates an example operating room environment including a surgical robotic system.

FIG. 1 is a diagram illustrating an example operating room environment with a surgical robotic system 100. As shown in FIG. 1, the surgical robotic system 100 comprises a user console 110, a control tower 130, and a surgical robot 120 having one or more surgical robotic arms 122 mounted on a surgical platform 124 (e.g., a table or a bed etc.), where surgical tools with end effectors are attached to the distal ends of the robotic arms 122 for executing a surgical procedure. The robotic arms 122 are shown as table-mounted, but in other configurations, the robotic arms may be mounted in a cart, a ceiling, a sidewall, or other suitable support surfaces.

Generally, a user, such as a surgeon or other operator, may be seated at the user console 110 to remotely manipulate the robotic arms 122 and/or surgical instruments (e.g., teleoperation). The user console 110 may be located in the same operation room as the robotic system 100, as shown in FIG. 1. In other environments, the user console 110 may be located in an adjacent or nearby room, or teleoperated from a remote location in a different building, city, or country. The user console 110 may comprise a seat 112, pedals 114, one or more handheld user interface devices (UIDs) 116, and an open display 118 configured to display, for example, a view of the surgical site inside a patient. As shown in the exemplary user console 110, a surgeon sitting in the seat 112 and viewing the open display 118 may manipulate the pedals 114 and/or handheld user interface devices 116 to remotely control robotic arms 122 and/or surgical instruments mounted to the distal ends of the arms 122.

In some variations, a user may also operate the surgical robotic system 100 in an "over the bed" (OTB) mode, in which the user is at the patient's side and simultaneously manipulating a robotically-driven tool/end effector attached thereto (e.g., with a handheld user interface device 116 held in one hand) and a manual laparoscopic tool. For example, the user's left hand may be manipulating a handheld user interface device 116 to control a robotic surgical component, while the user's right hand may be manipulating a manual laparoscopic tool. Thus, in these variations, the user may perform both robotic-assisted minimally invasive surgery (MIS) and manual laparoscopic surgery on a patient.

An end effector may be configured to execute a surgical operation such as cutting, grasping, poking, or energy emission. The surgical tool may be manipulated manually, robotically, or both, during the surgery. For example, the surgical tool may be a tool used to enter, view, or manipulate an internal anatomy of the patient. In an embodiment, the surgical tool is a grasper that can grasp tissue of the patient. The surgical tool may be controlled manually, directly by a hand of a bedside operator or it may be controlled robotically, via sending electronic commands to actuate movement.

During an exemplary procedure or surgery, the patient is prepped and draped in a sterile fashion to achieve anesthesia. Initial access to the surgical site may be performed manually with the robotic system 100 in a stowed configuration or withdrawn configuration to facilitate access to the surgical site. Once the access is completed, initial positioning and/or preparation of the robotic system may be performed. During the procedure, a surgeon in the user console 110 may utilize the pedals 114 and/or user interface devices 116 to manipulate various end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 122. Nonsterile personnel may also be present to assist the surgeon at the user console 110. When the procedure or surgery is completed, the robotic system 100 and/or user console 110 may be configured or set in a state to facilitate one or more post-operative procedures, including but not limited to, robotic system 100 cleaning and/or sterilization, and/or healthcare record entry or printout, whether electronic or hard copy, such as via the user console 110.

In some aspects, the communication between the surgical robot 120 and the user console 110 may be through the control tower 130, which may translate user input from the user console 110 to robotic control commands and transmit the control commands to the surgical robot 120. The control tower 130 may also transmit status and feedback from the robot 120 back to the user console 110. The connections between the surgical robot 120, the user console 110 and the control tower 130 may be via wired and/or wireless connections, and may be proprietary and/or performed using any of a variety of data communication protocols. Any wired connections may be optionally built into the floor and/or walls or ceiling of the operating room. The surgical robotic system 100 may provide video output to one or more displays, including displays within the operating room, as well as remote displays accessible via the Internet or other networks. The video output or feed may also be encrypted to ensure privacy and all or portions of the video output may be saved to a server or electronic healthcare record system.

Prior to initiating surgery with the surgical robotic system, the surgical team can perform the preoperative setup. During the preoperative setup, the main components of the surgical robotic system (table 124 and robotic arms 122, control tower 130, and user console 110) are positioned in the operating room, connected, and powered on. The surgical platform 124 and robotic arms 122 may be in a fully-stowed configuration with the arms 122 under the surgical platform 124 for storage and/or transportation purposes. The surgical team can extend the arms from their stowed position for sterile draping.

After draping, the arms 122 can be partially retracted until needed for use. A number of conventional laparoscopic steps may be performed including trocar placement and installation. For example, each sleeve can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars.

After insufflation, if required, manual instruments can be inserted through the sleeve to perform any laparoscopic steps by hand. Next, the surgical team may position the robotic arms 122 over the patient and attach each arm 122 to its corresponding sleeve. The surgical robotic system 100 has the capability to uniquely identify each tool (endoscope and surgical instruments) as soon as it is attached and display the tool type and arm location on the open or immersive display 118 at the user console 110 and the touchscreen display on the control tower 130. The corresponding tool functions are enabled and can be activated using the master UIDs 116 and foot pedals 114. The patient-side assistant can attach and detach the tools, as required, throughout the procedure. The surgeon seated at the user console 110 can begin to perform surgery using the tools controlled by two master UIDs 116 and foot pedals 114. The system translates the surgeon's hand, wrist, and finger movements through the master UIDs 116 into precise real-time movements of the surgical tools. Therefore, the system constantly monitors every surgical maneuver of the surgeon and pauses instrument movement if the system is unable to precisely mirror the surgeon's hand motions. In case the endoscope is moved from one arm to another during surgery, the system can adjust the master UIDs 116 for instrument alignment and continue instrument control and motion. The foot pedals 114 may be used to activate various system modes, such as endoscope control and various instrument functions including monopolar and bipolar cautery, without involving surgeon's hands removed from the master UIDs 116.

The surgical platform 124 can be repositioned intraoperatively. For safety reasons, all tooltips should be in view and under active control by the surgeon at the user console 110. Instruments that are not under active surgeon control are removed, and the table feet are locked. During table motion, the integrated robotic arms 122 may passively follow the table movements. Audio and visual cues can be used to guide the surgery team during table motion. Audio cues may include tones and voice prompts. Visual messaging on the displays at the user console 110 and control tower 130 can inform the surgical team of the table motion status.

Figure 2:
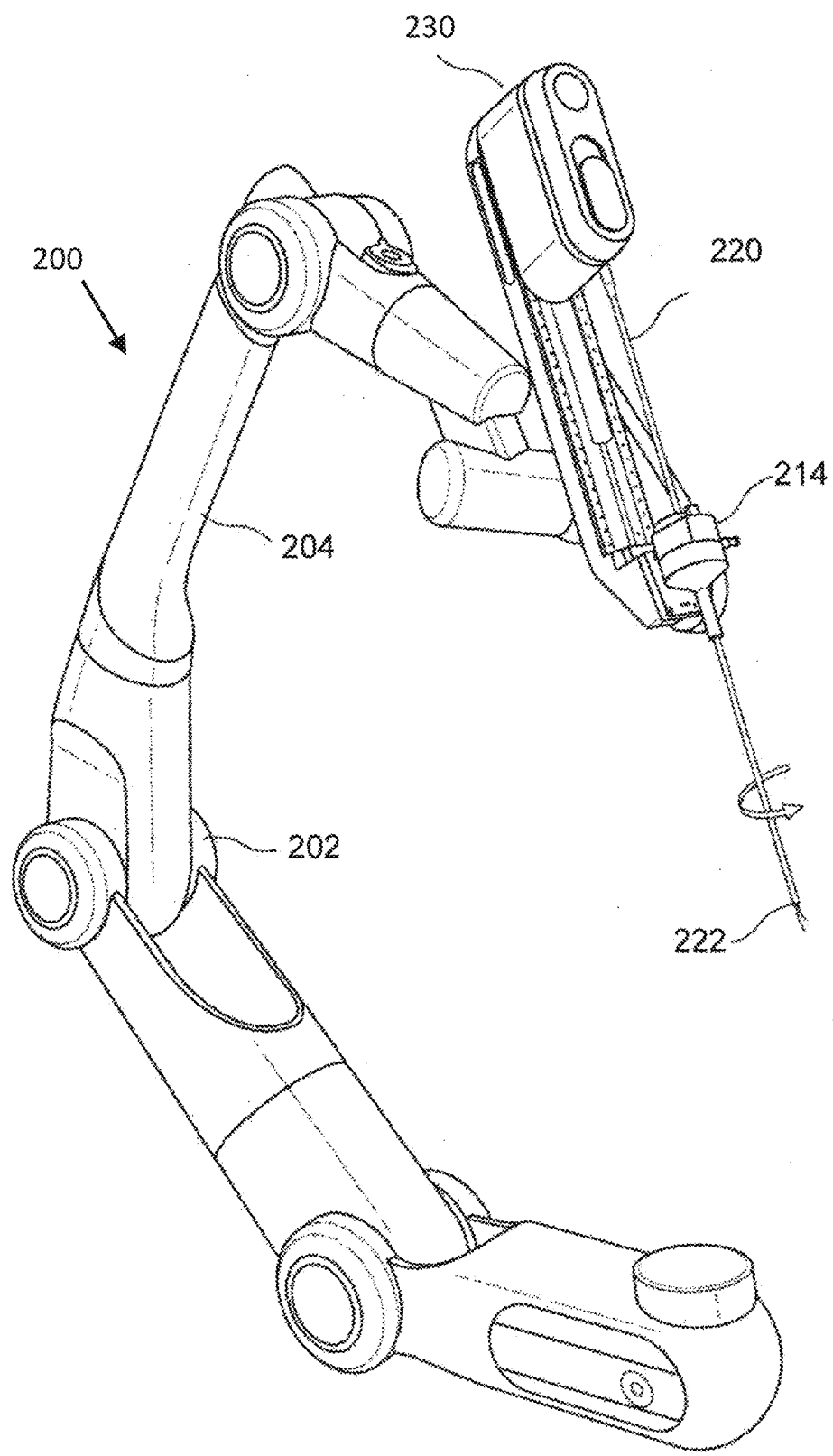
FIG. 2 illustrates an example surgical robotic system including a robotic arm, a tool driver, and a cannula loaded with a surgical tool.

FIG. 2 is a schematic diagram illustrating one exemplary design of a robotic arm, a tool driver, and a cannula loaded with a robotic surgical tool. As shown in FIG. 2, the example surgical robotic arm 200 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool driver 230 attached to the distal end of the robotic arm 200. The tool driver 230 may include a cannula 214 coupled to its end to receive and guide a surgical instrument (e.g. such as endoscopes, staplers, etc.). The surgical instrument 220 (or "tool") may include an end effector 222 at the distal end of the tool 220. The plurality of the joint modules of the robotic arm 200 can be actuated to position and orient the tool driver 230, which actuates the tool 220 for robotic surgeries.

Figure 3A:
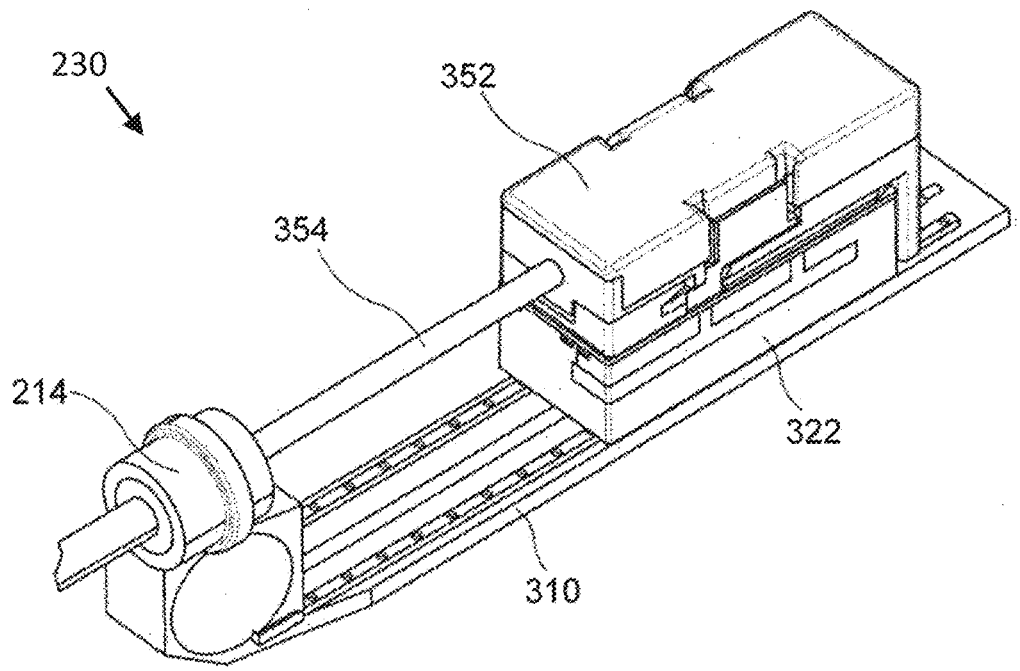
FIG. 3A illustrates an exemplary tool driver with a loaded surgical tool.
Figure 3B:
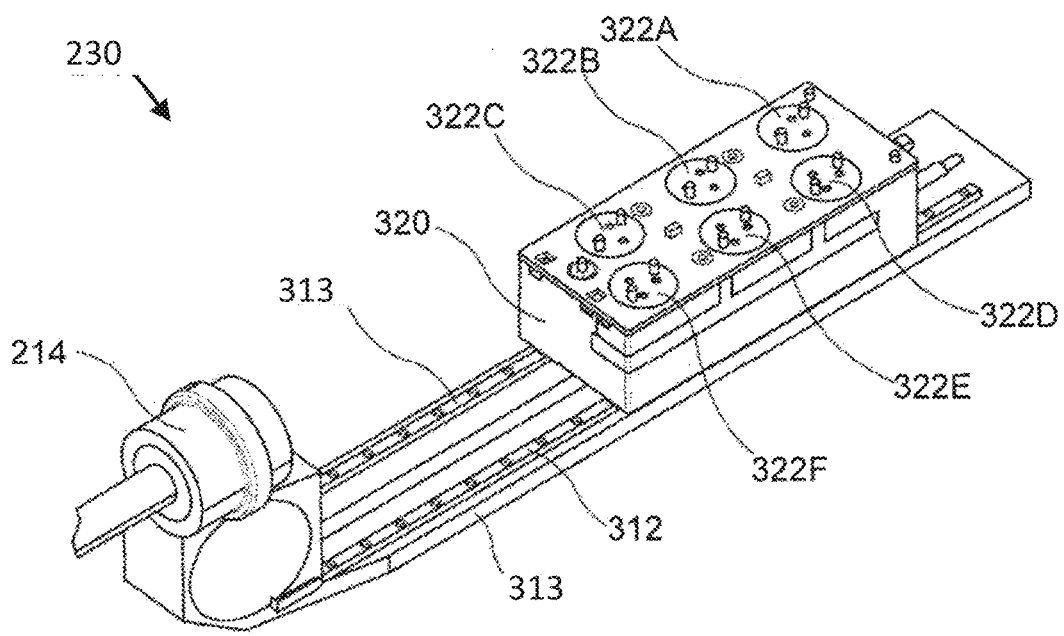
FIG. 3B illustrates an exemplary tool driver without a loaded surgical tool.

FIGS. 3A and 3B are schematic diagrams illustrating an exemplary tool driver with and without a loaded tool adjacent, respectively, in accordance with aspects of the subject technology. As shown in FIGS. 3A and 3B, in one variation, the tool driver 230 may include an elongated base (or "stage") 310 having longitudinal tracks 313 and a tool carriage 320, which is slidingly engaged with the longitudinal tracks 313. The stage 310 may be configured to couple to the distal end of a robotic arm such that articulation of the robotic arm positions and/or orients the tool driver 230 in space. Additionally, the tool carriage 320 may be configured to receive a tool base 352 of the tool, which may also include a tool shaft 354 extending from the tool base 352 and through the cannula 214, with the end effector 222 disposed at the distal end.

Additionally, the tool carriage 320 may actuate a set of articulated movements of the end effector, such as through a cable system or wires manipulated and controlled by actuated drives. The tool carriage 320 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 320 may include six rotary drives 322A-322F arranged in two rows, extending longitudinally along the base that are slightly staggered to reduce width of the carriage and increase the compact nature of the tool driver. As shown in FIG. 3B, rotary drives 322A, 322B, and 322C may be generally arranged in a first row, while rotary drives 322D, 322E, and 322F may be generally arranged in a second row that is slightly longitudinally offset from the first row.

Figure 4B:
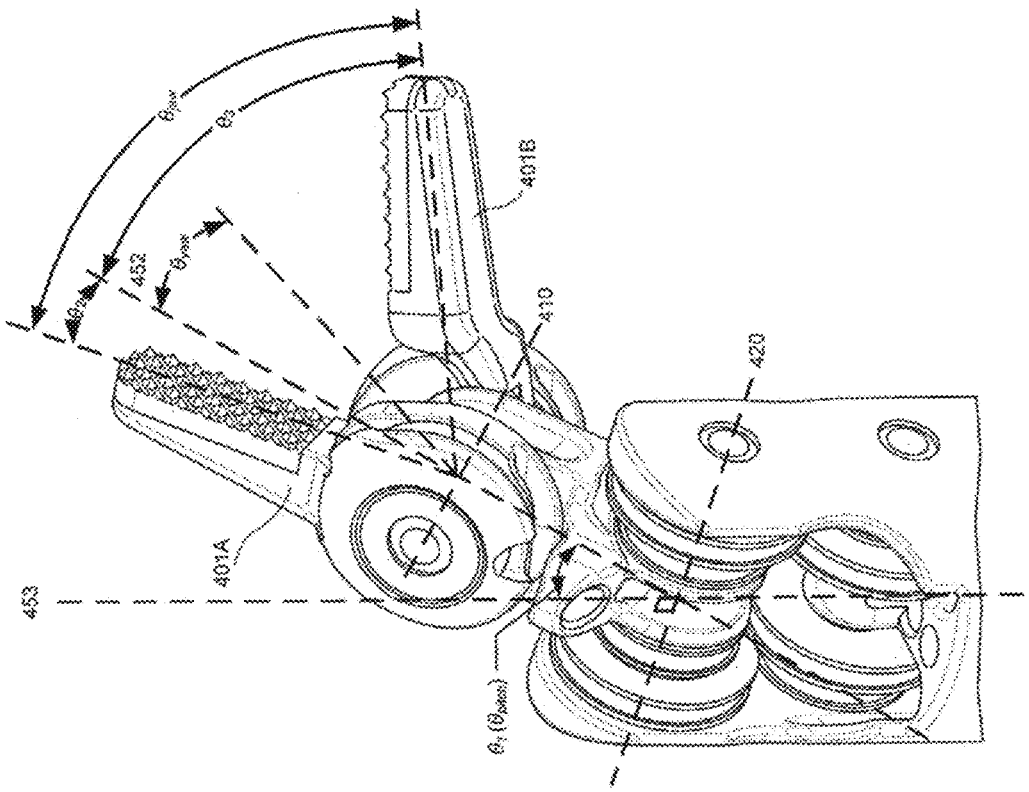
FIGS. 4A and 4B illustrate an end effector of an exemplary grasper having a robotic wrist, a pair of opposing jaws, and a pulley and cable system for coupling the robotic wrist and the pair of jaws to the actuators of a tool driver.
Figure 4A:
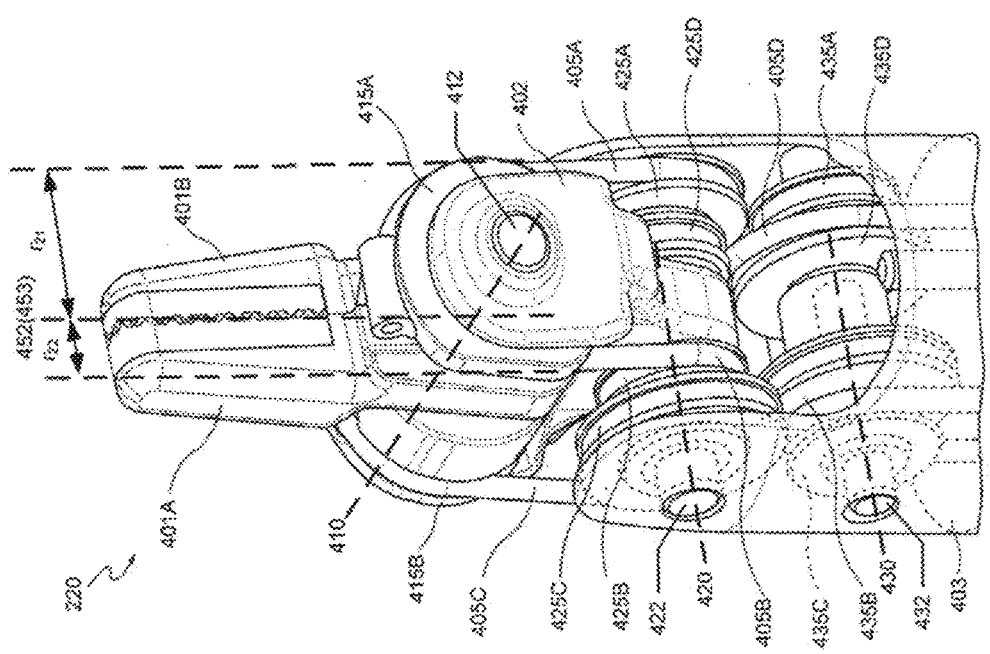

FIGS. 4A and 4B are schematic diagrams illustrating an end effector of an exemplary tool having a robotic wrist, a pair of opposing jaws, and a pulley and cable system for coupling the robotic wrist and the pair of jaws to actuators of a tool driver. Note that although the following tool model and controller design are described with reference to the exemplary surgical robotic grasper, the proposed control system for position and grip force control may be adapted to any tools that include an end effector coupled to a tool shaft via a robotic wrist, which allows multi-axial motion (e.g., pitch and yaw) of the end effector. Similar tools include, but not limited to, needle drivers, monopolar scissors, monopolar hook, bipolar forceps, and other instruments. A needle driver or needle holder includes opposing grippers for holding a needle and operates in a similar manner to the graspers (e.g. open/close, yaw, and pitch) described in detail herein. A set of monopolar scissors are double action scissors with curved plans that also operate in a similar manner to the graspers (e.g. open/close, yaw, and pitch). A set of bipolar forceps includes two tips designed to grasp, manipulate and coagulate selected tissue and also operate in a similar manner to the graspers (e.g. open/close, yaw, and pitch).

As shown in FIG. 4A, the pair of opposing jaws 401A and 401B are movably coupled to a first yoke 402 of the robotic wrist via an extended axle 412 along a first axis 410. The first yoke 402 may be movably coupled to a second yoke 403 of the robotic wrist via a second extended axle 422 along a second axis 420. The pair of jaws 401A and 401B may each be coupled or integrally formed with pulleys 415A and 415B respectively, via the extended axle 412, so that both jaws can rotate about the axis 410. Pulleys 425A, 425B, 425C and 425D are coupled to the extended axle 422 and rotate around the axis 420. The pulleys 425A, 425B, 425C and 425D are arranged into a first set of pulleys 425B and 425C on one side of the yoke 402 and a second set of pulleys 425A and 425D on the other side of the yoke 402. The pulleys 425A and 42C are outer pulleys and the pulleys 425B and 425D are inner pulleys. Similarly, the third set of pulleys 435A, 435B, 435C and 435D are coupled to a third extended axle 432 and rotate around the axis 430, which is parallel to the axis 420.

The end effector 222 (grasper) can be actuated to move one or both of the jaws 401A and 401B in a variety of ways around the axis 410. For example, the jaws 401A and 401B may open and close relative to each other. The jaws 401A and 401B may also be actuated to rotate together as a pair to provide a yaw motion of the end effector 222 (grasper). In addition, the first yoke 402, the pulleys 415A and 415B, and the jaws 401A and 401B can rotate about the axis 420 to provide a pitch motion of the end effector 222 (grasper). These motions of the robotic wrist and/or the jaws of the tool can be affected by controlling four independent cables 405A-405D. As shown in FIG. 4A, cable 405A may start (or terminates) from one side of the pulley 415A and route along pulleys 425A and 435A, and cable 405B is configured to terminate at the other side of the pulleys 415A and route through pulleys 425B and 435B. Similarly, another pair of cables 405C and 405D can be coupled to the jaw 401B. For example, cable 405C extends from one side of the pulley 415B to pulleys 425C and 435C; and cable 405D routes through pulleys 425D and 435D and terminates at the other side of pulley 415B. The third set of pulleys 435A, 435B, 435C and 435D are arranged in such a way as to keep the cables 405A-405D affixing to the second set of pulleys 425A-425D and prevent the cables from slipping or sliding relative to the pulleys 425A-425D.

Controlling the motions of the end effector 222 (grasper) via four independent cables has several advantages. One advantage may be the reduction of the number of cables that extend from the tool base 352 to the robotic wrist compared to typical on-market designs using six cables (or three cable loops with six cable ends). Less number of cables can reduce the tool size as well as complexity of the wrist assembly, which may benefit minimally-invasive surgical procedures or non-surgical applications. Furthermore, arrangement of four independent cables instead of two or three cable loops not only allows independent control of the tension on each cable without the need for pre-tensioning of the cables, but also enables variable compliance in the wrist joints and increased sensitivity to external loads. Additionally, it is possible to readjust tension on each cable independently, which can further increase tool performance.

As shown in FIGS. 4A and 4B, the end effector 222 (grasper) can be actuated to move the jaws 401A and 401B in a variety of ways such as grasping (e.g., jaws rotating independently about axis 410), yaw (e.g., jaws rotating together about axis 410), and pitch (e.g., jaws rotating about axis 420) by imparting motion to one or more of the pulleys 415A, 415B, 425A, 425B, 425C, and 425D to thereby impart motion on the first yoke 402 and/or one or both of the jaws 401A and 401B. Cables 405A-405D can be grouped into two antagonistic pairs, that is, when one cable of the antagonistic pair is actuated or tensioned, while the other cable is loosened, the jaw will rotate in one direction. Whereas when only the other cable is tensioned, the jaw will rotate in an opposite direction.

For example, cables 405A and 405B are the first antagonistic pair for moving jaw 401A, and cables 405C and 405D are the second antagonistic pair for controlling jaw 401B. When cable 405A is tensioned (e.g., by at least one of the rotary drives 322A-322F) while cable 405B is loosened, jaw 401A closes (moving towards the opposite jaw 401B). On the other hand, when cable 405B is tensioned and cable 405A is loosened, jaw 401A opens (moving away from the opposite jaw 401B). Similarly, when tensioned, cable 405C closes jaw 401B (moving towards the opposite jaw 401A) and cable 405D opens jaw 401B (moving away from the opposite jaw 401A) while the other cable loosens. As another example, grip force between the jaw 401A and jaw 401B can be achieved by continuing to tension both cable 405A and cable 405C (while cable 405B and cable 405D are loosened) after the jaws are closed (touching each other).

In case when both cables of an antagonistic pair are tensioned at the same time while both cables of the other pair are loosened, the pulley 415A or pulley 415B do not rotate. Instead, the first yoke 402 together with the jaws 401A and 401B are imparted by the pulleys 415A and 415B to pitch about the axis 420. For example, when the pair of cables 405A and 405B are both tensioned simultaneously while the pair of cable 405C and 405D are loosened, the jaws (together with the yoke 402) pitch out of the plane of the paper. Whereas when both cables 405C and 405D are tensioned simultaneously and the pair 405A and 405B are kept loose, the jaws pitch into the plane of the paper.

FIG. 4B is a schematic diagram illustrating example angle definitions for various motions of the end effector 221 (grasper). The angles are defined in reference to axes 410 and 420, as well as an axis 452 of the first yoke 402 and an axis 453 of the second yoke 403. For example, as shown in FIG. 4B, an angle ($\theta_1$) between axis 452 and the axis 453 may represent the rotation angle of the yoke 402 around axis 420, which may also be defined as the pitch angle ($\theta_{pitch}$) of the end effector 222 (grasper) (while in FIG. 4A, the axis 452 of the yoke 402 is superimposed over the axis 453 of the yoke 403 because the jaws are staying in the reference position, i.e., no pitch motions). In addition, angles ($\theta_2$) and ($\theta_3$) can represent the angles between each of the jaws 401A and 401B and the axis 452 of the yoke 402 (as the origin), respectively. To differentiate the sides of the axis 452, angles ($\theta_2$) and ($\theta_3$) may take on different signs. For example, angle ($\theta_2$) is negative and angle ($\theta_3$) is positive, as illustrated in FIG. 4B.

In order to perform control tasks, it is often beneficial to define a consistent coordinate frame for the joint angles. For example, the jaw angle ($\theta_{jaw}$) may be defined as the angle between the two jaws 401A and 401B, and the yaw angle ($\theta_{yaw}$) may be defined as the angle between the axis 452 and the line bisecting the jaw angle. These angles may be defined according to Equations 1-3:

$$\theta_{pitch} = \theta_1 \qquad \text{Eq. 1}$$

$$\theta_{yaw} = \tfrac{1}{2}(\theta_2 + \theta_3) \qquad \text{Eq. 2}$$

$$\theta_{jaw} = \theta_2 - \theta_3 \qquad \text{Eq. 3}$$

The transformation between angles in FIG. 4B and the defined angles are as described in Equation 4:

$$\begin{bmatrix} \theta_{pitch} \\ \theta_{yaw} \\ \theta_{jaw} \end{bmatrix} = \begin{bmatrix} 1 & 0 & 0 \\ 0 & \tfrac{1}{2} & \tfrac{1}{2} \\ 0 & 1 & -1 \end{bmatrix} \begin{bmatrix} \theta_1 \\ \theta_2 \\ \theta_3 \end{bmatrix} \qquad \text{Eq. 4}$$

Furthermore, the following nomenclature can be established for pulley geometries:

a) r11 is the radius of the outer pulleys 425A and 425C on which cables 405A and 405C are residing, respectively;

b) r12 is the radius of the inner pulleys 425B and 425D on which cables 405B and 405D are residing, respectively (r11 may or may not be equal to r12);

c) r21 is the radius of pulley 415A on the side that cable 405A is residing (with reference to the center of pulley 415A and axle 412 as shown in FIG. 4A);

d) r22 is the radius of pulley 415A on the side that cable 405B is residing (with reference to the center of pulley 415A and axle 412 as shown in FIG. 4A);

e) r31 is the radius of pulley 415B on the side that cable 405C is residing; and f) r32 is the radius of pulley 415B on the side that cable 405D is residing.

While in the above example symmetrical design, r31=r21, r32=r22 and r21 (as shown in FIG. 4A), in some other designs it is possible to have r31=r21=r32=r22, as well as r11=r12.

The fundamental equation that relates cable tensions ($\xi$[4×1]) to joint torques ($\tau$[3×1]) is presented by Equation 5:

$$\tau[3\times 1] = B[3\times 4]\cdot\xi[4\times 1] \qquad \text{Eq. 5}$$

where matrix (B) has the form given by Equation 6:

$$B = [-r_{11} -r_{12} r_{11}\ r_{12} -r_{21}\ r_{22}\ 0\ 0\ 0\ 0\ r_{31} -r_{32}] \qquad \text{Eq. 6}$$

The kinematic relationship that relates the ideal cable displacements (assuming no cable elasticity) and jaw angles are described in Equation 7:

$$q_{[4\times 1]} = B^T{}_{[4\times 3]} \theta_{[3\times 1]} \qquad \text{Eq. 7}$$

Here $q = [q_1\ q_2\ q_3\ q_4]^T$ is the displacement of cables in the ideal case where the cables are rigid. Therefore, the relationships in expanded form are described as Equation(s) 8:

$$q_1 = -r_{11}\theta_1 - r_{21}\theta_2$$

$$q_2 = -r_{12}\theta_1 + r_{22}\theta_2\ q_3 = +r_{11}\theta_1 + r_{31}\theta_3\ q_4 = +r_{12}\theta_1 - r_{31}\theta_3$$

where $\theta_1$ is the pitch joint angle, and $\theta_2$ and $\theta_3$ are the joint angles of jaw A and jaw B, respectively (see FIG. 3). In reality, the cables may be somewhat elastic and the cable forces and elongation follow the Hooke's law as shown in Equation(s) 9:

$$\xi_1 = k(x_1 - q_1)$$

$$\xi_2 = k(x_2 - q_2) \quad \xi_3 = k(x_3 - q_3) \quad \xi_4 = k(x_4 - q_4)$$

where k is cable elasticity (assuming the four cables are similar), and x is the actuator displacements. The actuator displacements then may be related to the joint angles for the end effector 222 in two different coordinate frames.

If the cables cannot be assumed to be elastic, the above equations may be replaced with the nonlinear equation relating the cable elongation and force.

The angular position and grip force of a distal end effector of a robotic surgical instrument. The end effector may include a robotic wrist and a pair of opposing members (e.g., jaws or claws), each being movable between an open position and a closed position actuated by two antagonistic cables. A total of four cables may each be driven by an independent actuator or motor. The control system may include feedback loops involving position and velocity feedback from the actuators and force feedback measured on the four cables, to effect desired position and grip force. In some implementations, the actuator controllers may be running a position plus feedforward current mode. For example, a position controller may drive the distal end effector to the desired angular position in space based on the positional feedback, while a grip force controller provides additional feedforward current based on the grip force measured by load cells on the four cables to achieve the desired grip force between the opposing members.

Figure 5:
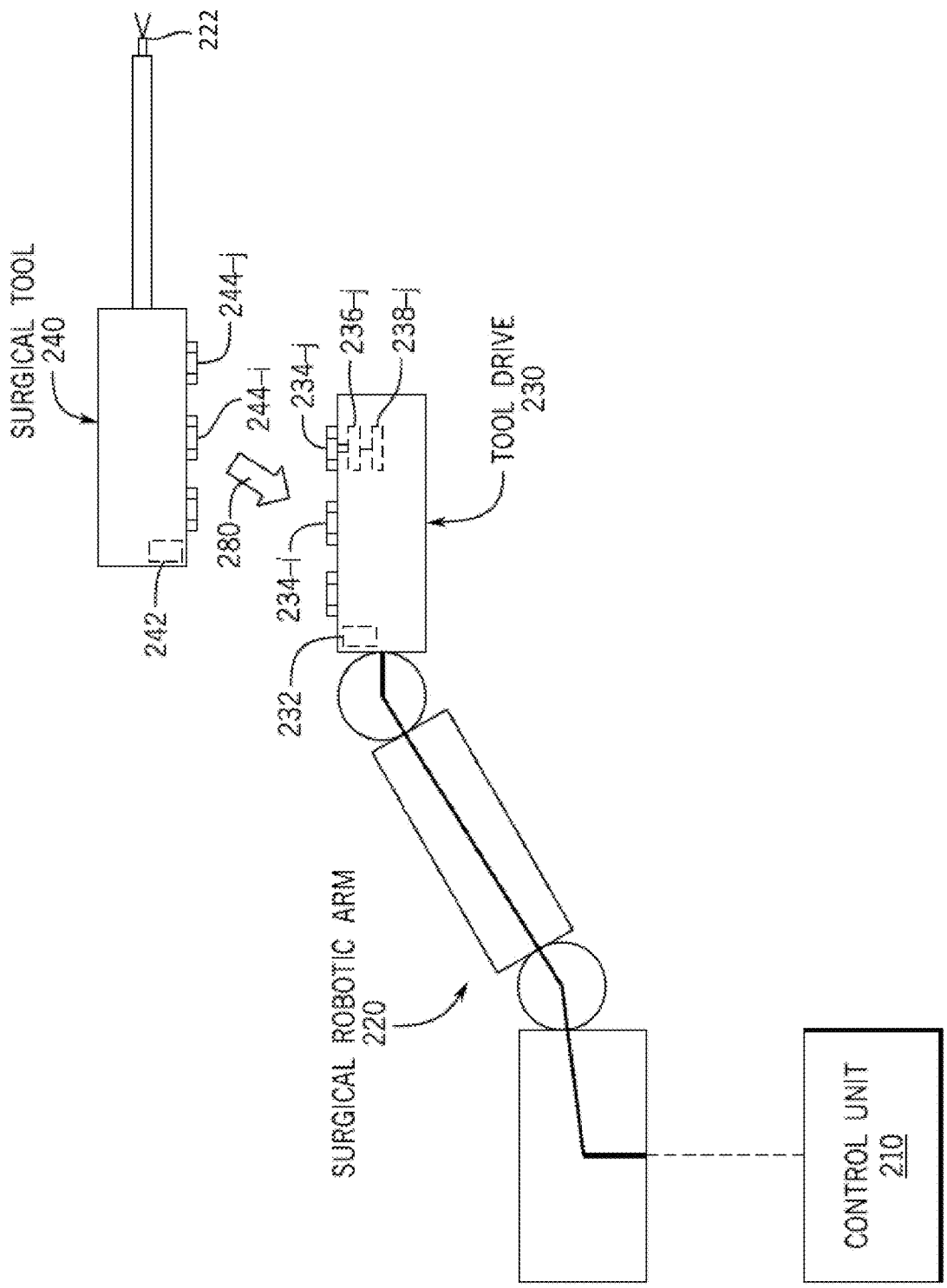
FIG. 5 illustrates a controller for the robotic wrist, tool driver and/or surgical tool.

FIG. 5 is an illustration of a subsystem or a part of the surgical robotic system 100, for detecting engagement of a surgical tool 240 to a tool driver 230 (tool driver) of a surgical robotic arm 122. The surgical robotic arm 122 may be one of the surgical robotic arms of surgical robotic system 100 illustrated and discussed with respect to FIG. 1. The control unit 210 may be part of for example the control tower in FIG. 1. As discussed in more detail herein, the engagement may be detected by control unit 210 based on one or more rotary motor operating parameters of one or more actuators (e.g., actuator 238-j) in the tool driver 230.

There is a tool driver 230 to which different surgical tools (e.g., surgical tool 240, as well as other detachable surgical tools for rotation of an endoscope camera, pivoting of a grasper jaw, or translation of a needle) may be selectively attached (one at a time.) This may be done by for example a human user holding the housing of the surgical tool 240 in her hand and moving the latter in the direction of arrow 280 shown until the outside surface of the surgical tool 240 in which there are one or more tool disks (e.g., tool disk 244-i) comes into contact with the outside surface of the tool driver 230 in which there are one or more drive disks (e.g., drive disk 234-j). The one or more tool disks and/or one or more drive disks may be implemented by pucks, which may be formed of plastic or another durable material. In the example shown, the tool driver 230 is a segment of the surgical robotic arm 122 at a distal end portion of the surgical robotic arm 122. A proximal end portion of the arm is secured to a surgical robotic platform, such as a surgical table that shown in FIG. 1 described above.

Control unit 210 is configured to control motion of the various motorized joints in the surgical robotic arm 122 (including the drive disks 234) through which operation of end effector 222 (its position and orientation as well as its surgical function such as opening, closing, cutting, applying pressure, etc.) which mimics that of a user input device is achieved. This is achieved via a mechanical transmission in the surgical tool 240, when the surgical tool 240 has been engaged to transfer force or torque from the tool driver 230. The control unit 210 may be implemented as a programmed processor, for example as part of the control tower 130 of FIG. 1. It may respond to one or more user commands received via a local or remote user input (e.g., joystick, touch control, wearable device, or other user input device communicating via console computer system.) Alternatively, the control unit 210 may respond to one or more autonomous commands or controls (e.g., received form a trained surgical machine learning model that is being executed by the control unit 210 or by the console computer system), or a combination thereof. The commands dictate the movement of robotic arm 122 and operation of its attached end effector 222.

An end effector 222 may be any surgical instruments, such as jaws (e.g., as shown in FIGS. 4A and 4B), a cutting tool, an endoscope, spreader, implant tool, etc. Different surgical tools each having different end effectors can be selectively attached (one at a time) to robotic arm 122 for use during a surgical or other medical procedure. The end effector 222 depicted in the example of FIG. 5 is jaws located at a distal end of the surgical tool 240 and that may be retracted into, or extend out of, a cannula as shown (e.g., a thin tube that may be inserted into a patient undergoing a surgical procedure).

The robotic arm 122 includes a tool driver 230, in which there are one or more actuators, such as actuator 238-j. Each actuator may be a linear or rotary actuator that has one or more respective electric motors (e.g., a brushless permanent magnet motor) whose drive shaft may be coupled to a respective drive disk 234-j through a transmission (e.g., a gear train that achieves a given gear reduction ratio). The tool driver 230 includes one or more drive disks 234 that may be arranged on a planar or flat surface of the tool driver 230, wherein the figure shows several such drive disks that are arranged on the same plane of the flat surface. Each drive disk (e.g., drive disk 234-j) is exposed on the outside surface of the tool driver 230 and is designed to mechanically engage (e.g., to securely fasten via snap, friction, or other mating features) a mating tool disk 244-j of the surgical tool 240, to enable direct torque transfer between the two. This may take place once for example a planar or flat surface of the surgical tool 240 and corresponding or mating planar or flat surface of the tool driver 230 are brought in contact with one another.

Furthermore, a motor driver circuit (for example, installed in the tool driver 230 or elsewhere in the surgical robotic arm 122) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-j).

When the mating drive disk 234-j is mechanically engaged to a respective tool disk 244-j, the powered rotation of the drive disk 234-j causes the tool disk 244-j to rotate, e.g., the two disks may rotate as one, thereby imparting motion on, for example, linkages, gears, cables, chains, or other transmission devices within the surgical tool 240 for controlling the movement and operation of the end effector 222 which may be mechanically coupled to the transmission device.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 222 to achieve goals such as load sharing by two or more motors that are driving the mating drive disks 234, respectively. In another aspect, within the tool driver 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complementary actions in the same degree of freedom, e.g., a first drive disk 234-*j* rotates a drum within the housing of the surgical instrument 240 to take in one end of a rod, and a second drive disk 234-*i* rotates another drum within the housing of the surgical instrument 240 to take in the other end of the rod. As another example, the extension and the shortening of an end effector along a single axis may be achieved using two tool disks 234-*i*, 234-*j*, one to perform the extension and another to perform the retraction. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 222 being jaws, two or more tool disks 244 may cooperatively control the motion of the jaws, for load sharing, as discussed in greater detail herein.

In yet another aspect, within the surgical tool 240, there may be a transmission which translates torque from two drive disks 234 (via respective tool disks 244) for performing complementary actions in the same degree of freedom, e.g., a first drive disk 234-*i* rotates a drum within the housing of the surgical tool 230 to take in one end of a cable, and a second drive disk 234-*j* rotates another drum within the housing of the surgical tool 230 to take in the other end of the cable. As another example, the extension and the shortening of an end effector along a single axis may be achieved using two tool disks 234-*i*, 234-*j*, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

Figure 6:
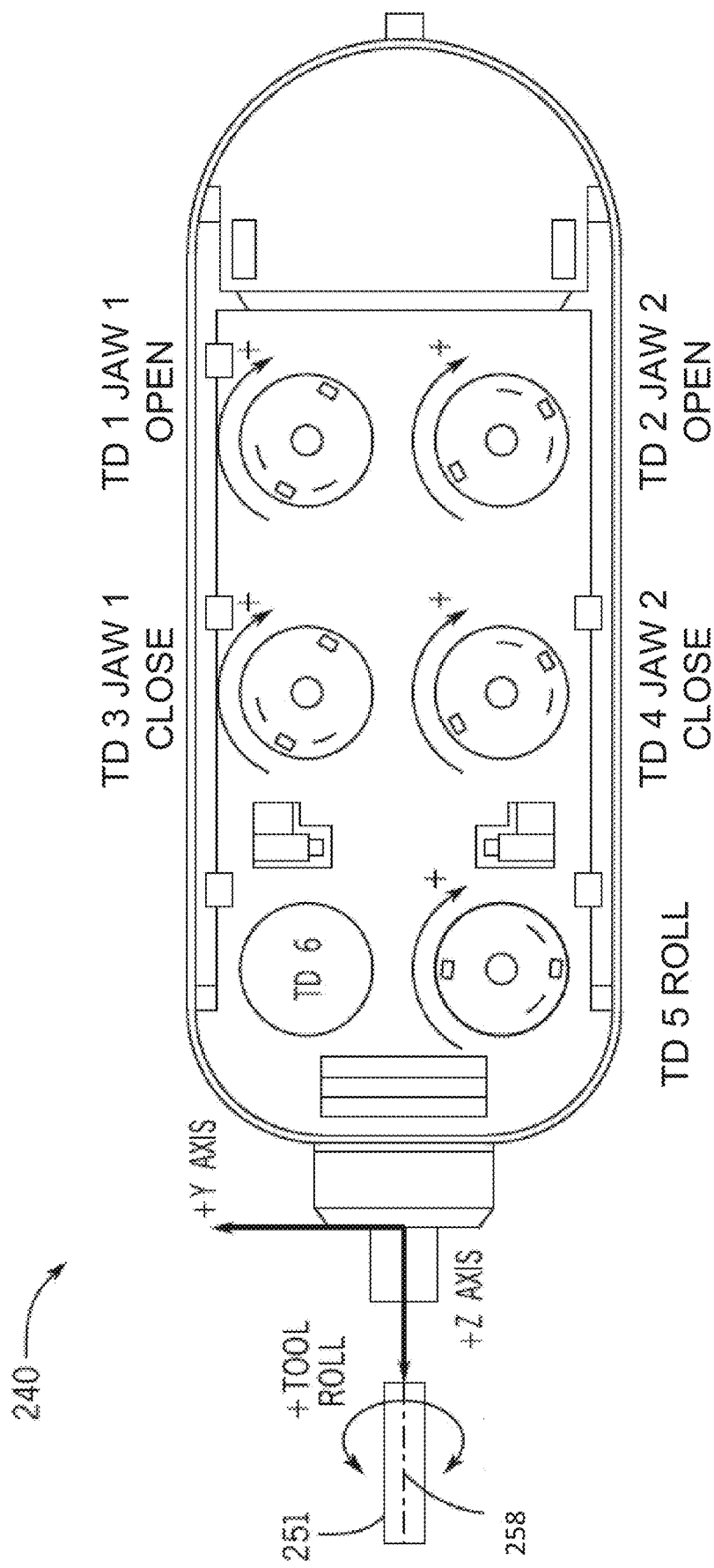
FIG. 6 illustrates a mapping for the tool driver to the surgical tool.

FIG. 6 illustrates an example of the surgical tool 240 including rotary device assignments or mapping for tool disks TD1-5 (TD 6 is unused in this example). In this example, tool disk TD5 is mapped to the roll axis 258 of the end effector, which is illustrated as jaw 251 and may comprise a first opposing jaw 401A and a second opposing jaw 401B. The tool disk TD5 may be coupled to one or more gears that drive the wrist to rotate about the roll axis. Each opposing jaw is assigned two tool disks. For example, the first opposing jaw 401A may be assigned to tool disk TD1 for opening the jaw (i.e., increasing the angle between the first opposing jaw 401A and the second opposing jaw 401B) and tool disk TD3 for closing the jaw (i.e., decreasing the angle between the first opposing jaw 401A and the second opposing jaw 401B). The tool disk TD1 may be coupled to a cable that rotates pulley 415A in a first direction and the tool disk TD3 may be coupled to a cable for rotating pulley 415A in a second direction.

Similarly, the second opposing jaw 401B may be assigned to tool disk TD2 for opening the jaw (i.e., increasing the angle between the first opposing jaw 401A and the second opposing jaw 401B) and tool disk TD4 for closing the jaw (i.e., decreasing the angle between the first opposing jaw 401A and the second opposing jaw 401B). The tool disk TD2 may be coupled to a cable that rotates pulley 415B in a first direction and the tool disk TD4 may be coupled to a cable for rotating pulley 415B in a second direction.

In some embodiments, when surgical tool 240 is first attached to or installed on tool driver 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, radio frequency identification (RFID) tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-*e, f, g, h, i, j*), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool driver 230 may include a communication interface 232 (e.g., a memory writer, a near field communications, near field communication (NFC), transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool driver 230 may also include a corresponding sensor for each possible information storage unit that would be present in a given tool.

After surgical tool 240 is attached with tool driver 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool driver 230 is now deemed engaged with the tool). That is, attaching the surgical tool 240 with the tool driver 230 does not necessarily ensure the proper mating needed for mechanical engagement of tool disks with corresponding drive disks (e.g., due to misalignment of mating features). The engagement process may include activating one or more motors of an actuator (e.g., actuator 238-*j*) that drives a corresponding drive disk 234-*j*. Then, based on one or more monitored motor operating parameters of the actuator 238-*j*, while the latter is driving the drive disk 234-*j*, the mechanical engagement of the tool disk 244-*i* with a drive disk 234-*j* can be detected. This process may be repeated for every drive disk 234 (of the tool driver 230) that is expected to be currently attached to a respective tool disk 244 (e.g., as determined based on the tool disk information obtained for the particular surgical tool 240 that is currently attached.)

Upon detecting that a particular type of surgical tool 240 has been attached with the tool driver 230, the control unit 210 activates one or more actuators (e.g., motors) of the tool driver 230 that have been previously associated with that type of surgical tool 240. In some embodiments, each actuator that is associated with a corresponding drive disk 234 of surgical tool 240 may be activated simultaneously, serially, or a combination of simultaneous and serial activation.

Figure 7:
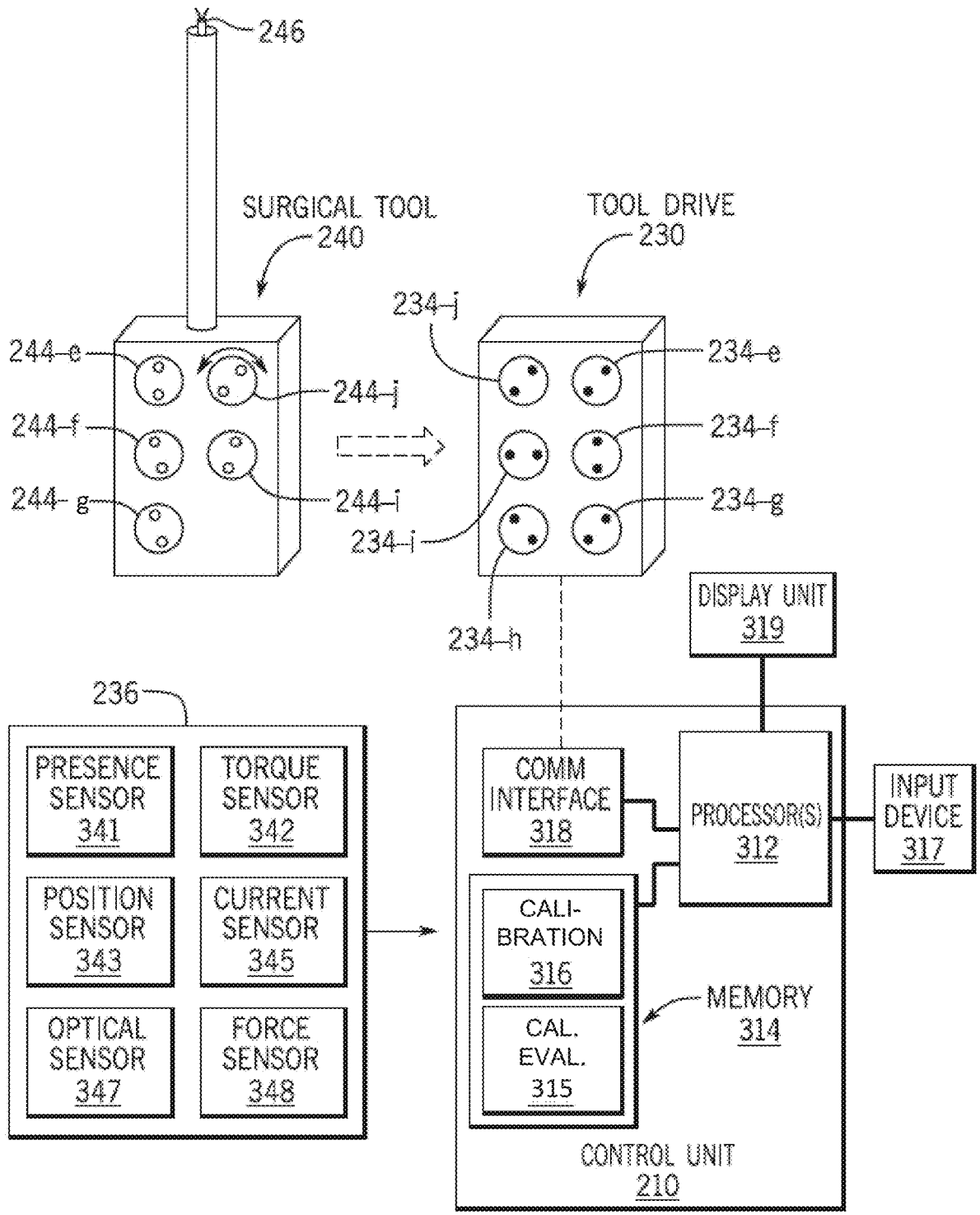
FIG. 7 illustrates a sensor array and a detailed embodiment of the controller.

FIG. 7 illustrates an example of the surgical tool 240 that utilizes five tool disks, such as tool disks 244-*e, f, g, i, j,* arranged in a coplanar fashion on a mating surface of its housing. Each tool disk contributes to at least a portion of the movement and/or activation of end effector 222. Upon detecting the attachment of surgical tool 240 with tool driver 230 (e.g., joining of mating surfaces of the respective housings), control unit 210 (or its processor 312 while executing instructions stored in memory 314 as calibration control 316) performs a process which determines that only the corresponding five drive disks, such as drive disks 234*e, f, g, i, j,* are to be turned (a corresponding actuator 238 is activated) to perform the engagement process.

In some embodiments, the motor operating parameters monitored by the control unit 210 (via sensors 236) are interpreted to mean successful mechanical engagement of a tool disk with a drive disk. The control unit 210 is in communication with and receives sensor data from sensor 236 in an example sensor array including any combination of a presence sensor 341, a torque sensor 342, a position sensor 343, an electrical sensor 345, an optical sensor 347, and a force sensor 348. The sensor array may include separate sensors for different degrees of freedom of the surgical tool (e.g., closure joint, roll joint, or other operation of the surgical tool). That is, the sensor array, or one or more sensors thereof, may be repeated for multiple tool disks 244 in the tool driver 230.

The measurements may include measurements of torque applied by the actuator 238-*j* as measured by the torque sensor 342 or the force sensor 348, measurements of current by the electrical sensor 345 supplied to a motor of the actuator 238-*j* when attempting to drive the actuator to move at a certain velocity (e.g., where the sensor 236-*j* may include a current sensing resistor in series with a motor input drive terminal), measurements of electrical impedance by the electrical sensor 345 as seen into the input drive terminals of the motor of the actuator 238 when attempting to drive the motor to move at a certain velocity (e.g., where the sensor 236-*j* may also include a voltage sensing circuit to measure voltage of the motor input drive terminal), speed of the actuator 238-*j* (e.g., where the optical sensor 347 may include a position encoder on an output shaft of the actuator 238-*j* or on a drive shaft of the motor), as well as other parameters referred to here as motor operating parameters. The measurements may include presence data from the presence sensor 341, implied from any sensor in the sensor array 236, or determined from the interaction between the information storage unit 242 and the communication interface 232. The position sensor 343 is illustrated separately but may be implemented using a combination of the presence sensor 341, the torque sensor 342, the electrical sensor 345, the optical sensor 347, and the force sensor 348. In one example, additional sensors of the same type may be used for the position sensor 343.

While monitoring the one or more motor operating parameters of a particular actuator, when one or more of these parameters satisfies (e.g., meets or reaches) a predetermined, condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-*j* or that is part of another actuator 238-*i* which his being controlled by the control unit 210 simultaneously during the engagement detection process.

In some embodiments, detection of certain motor operating parameters during operation of the actuator 238-*j*, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-*j* to drive disk 234-*j* has occurred. The following are some examples of such a process.

The control unit 210 including its programmed processor 312 may be integrated into the surgical robotic system 100 (FIG. 1) for example as a shared microprocessor and program memory within the control tower 130. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached surgical tool 240, a power device (e.g., a battery), as well as other components typically associated with electronic devices for controlling surgical robotic systems.

Memory 314 is coupled to one or more processors 312 (generically referred to here as a processor for simplicity) to store instructions for execution by the processor 312. In some embodiments, the memory is non-transitory, and may store one or more program modules, including a calibration algorithm 316 and a calibration evaluation algorithm 315, whose instructions configure the processor 312 to perform the calibration and calibration evaluation processes described herein. In other words, the processor 312 may operate under the control of a program, routine, or the execution of instructions stored in the memory 314 as part of the calibration algorithm 316 and the calibration evaluation algorithm 315 to execute methods or processes in accordance with the aspects and features described herein. The memory 314 may include one or more settings, coefficient values, threshold values, tolerance values, calibration values for the surgical tool 240 and/or the tool driver 230. These values may be stored in memory 314 as a configuration file, table, or matrix. Some values in the configuration file may be provided by the user, some may be accessed or retrieved based on identifiers of the surgical tool 240 or tool driver 230, and others may be set by the control unit 210.

Figure 8:
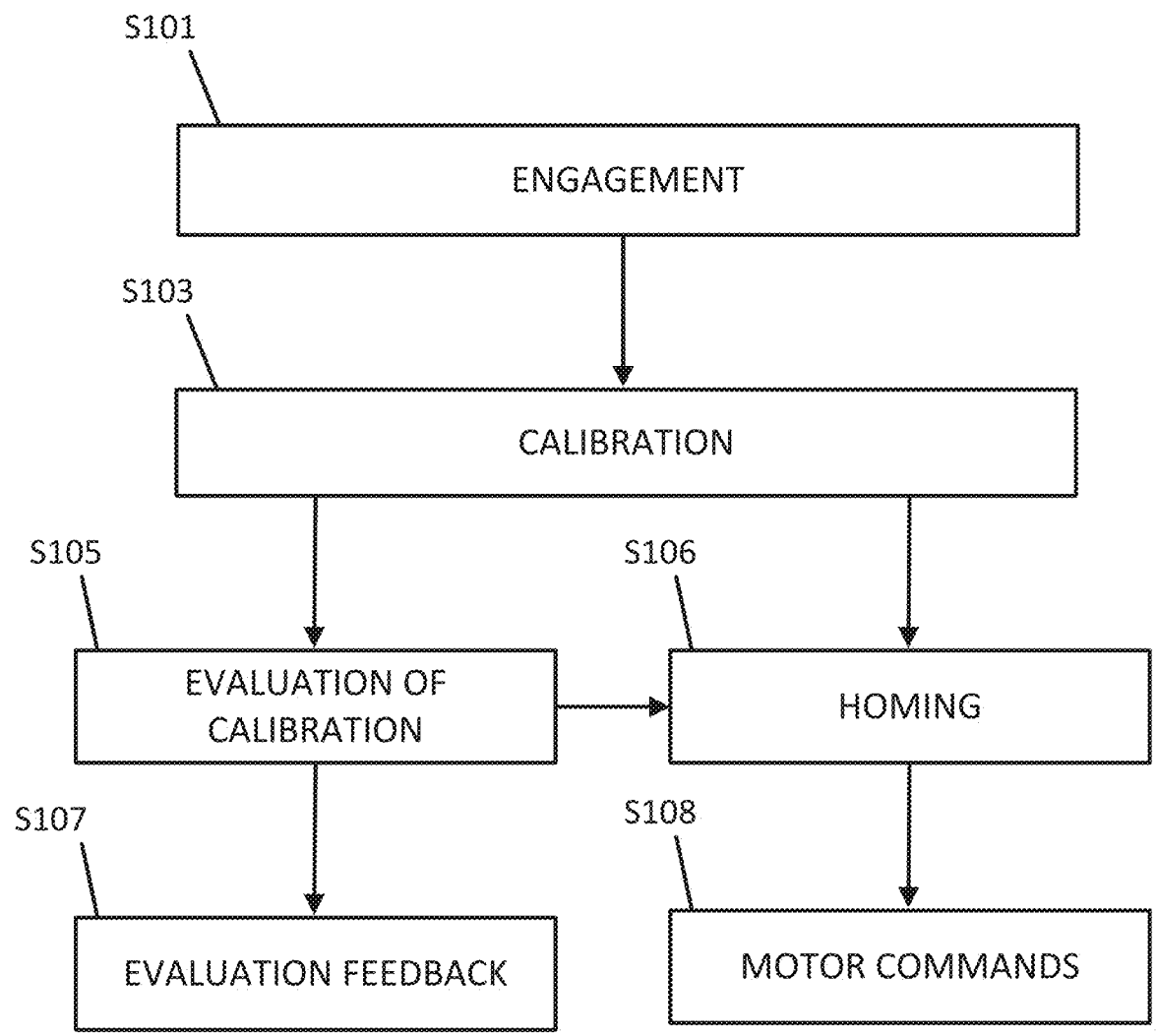
FIG. 8 illustrates an example flow chart for the controller.

FIG. 8 illustrates a procedure or technique that may be carried out by any of the systems described herein, for example, by a controller, such as the control unit 210. Each act in FIG. 8 may refer to a separate process that may have many steps. Additional, different, or fewer acts may be included.

At act S101, engagement is performed. The controller may facilitate the engagement of the surgical tool 240 to the tool driver 230 through the drive disks 234 and tool disks 244. The engagement process may include activating one or more motors of an actuator that drives a corresponding drive disk. The actuator 238 is monitored and the mechanical engagement of the tool disk 244 with a drive disk 234 can be detected (e.g., through data collected by one or more of torque sensor 342, position sensor 343, or another one of the sensor 236). This process may be repeated for every drive disk 234 (of the tool driver 230) that corresponds to the currently attached respective tool disk 244.

At act S103, calibration is performed, for example, by the calibration algorithm or instructions 316 stored in memory 314 and executed by control unit 210. The calibration process may set a homing position of the actuator 238 of the tool driver 230. The homing position may correspond to a zero position of the end effector 222 and/or jaws 401. Calibration may be performed in a variety of techniques. Calibration may involve placing the end effector 222 (e.g., jaws 401 and wrist) in a predetermined position. Once in the predetermined position, the corresponding position of the actuator 238 and/or motor may be measured.

The calibration may be implemented by a physical constraint technique or a camera technique. For the physical constraint technique for calibration, an external device is placed on the end effector 222 to hold it in place at the predetermined position.

Figure 9:
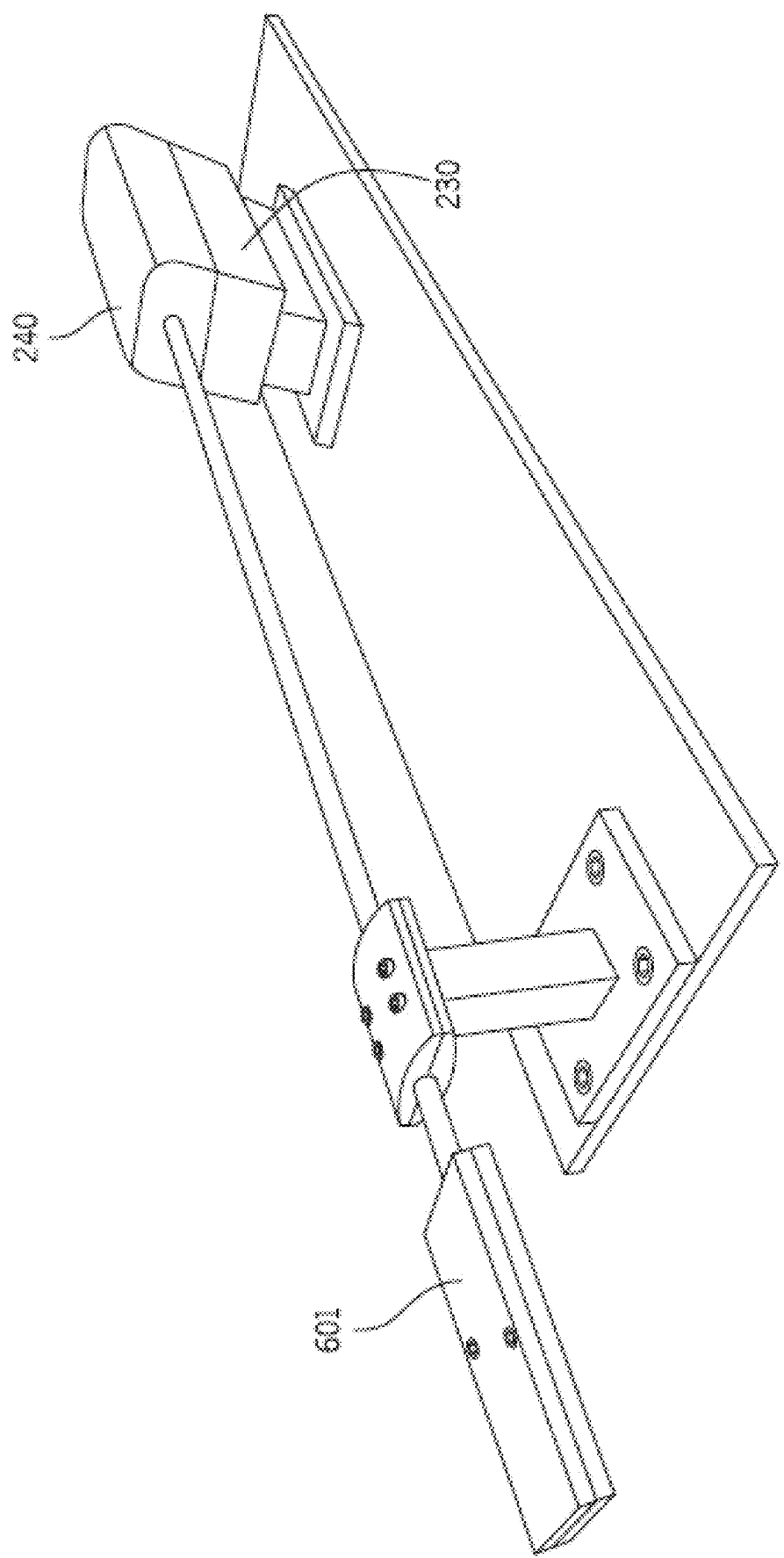
FIG. 9 illustrates an example of a tool driver and an end effector coupled to an external constraint.
Figure 10A:
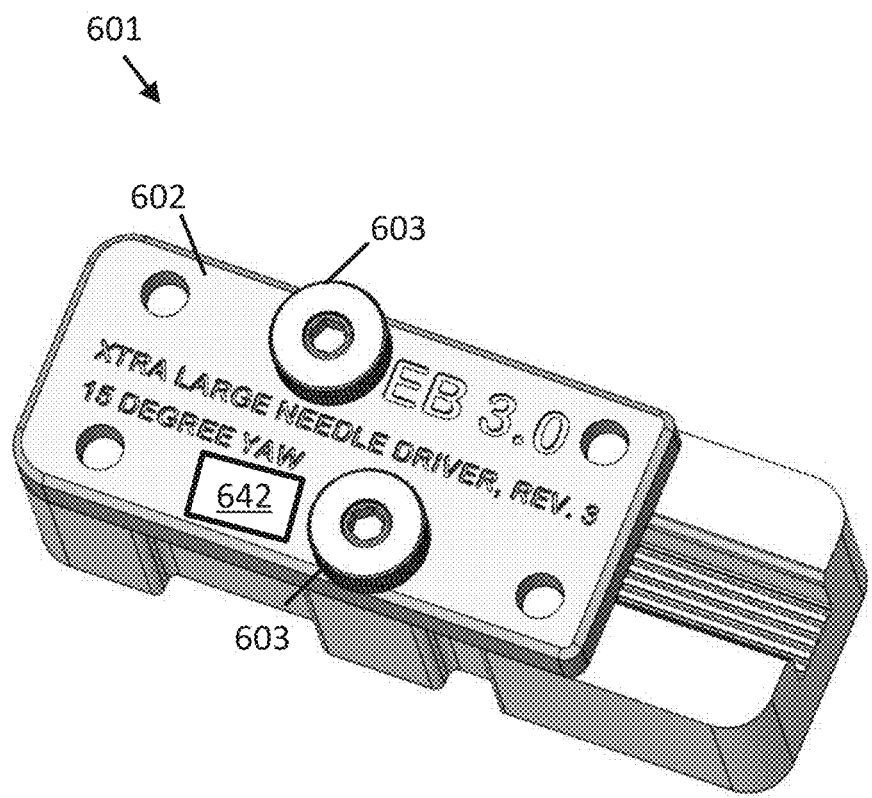
FIG. 10A illustrates an example external constraint.
Figure 10B:
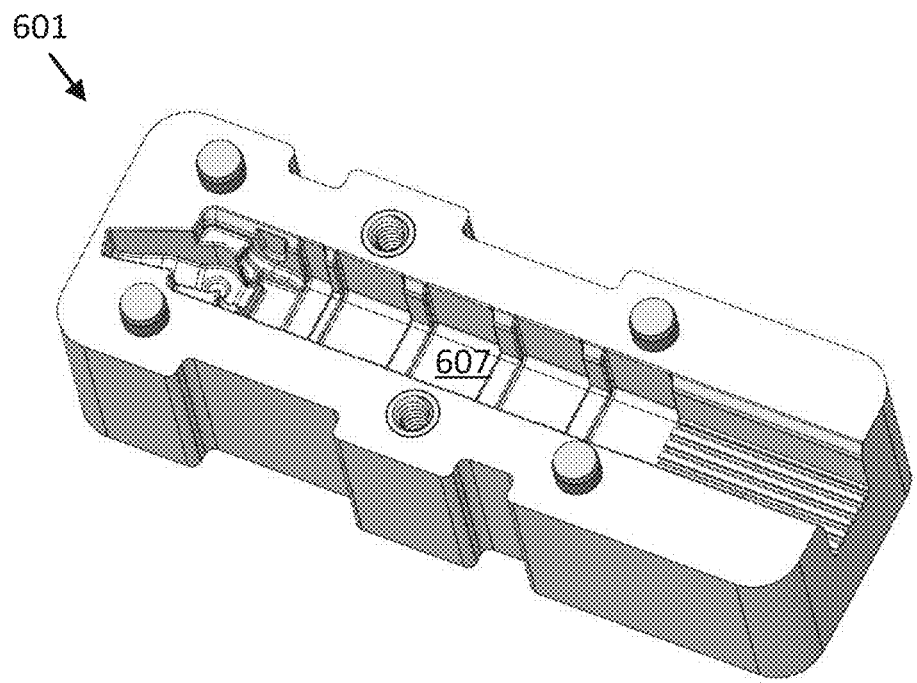
FIG. 10B illustrates the external constraint opened.

FIG. 9 illustrates an example of a tool driver 230 and an end effector 222 coupled to an external constraint 601. FIG. 10A illustrates an example external constraint 601, and FIG. 10B illustrates the external constraint with cover 602 removed to show cavity 607. The cover 602 may include indicia to describe the joint angles for the joint locker. The cover 602 may include identifier storage unit 642 to electronically store the joint angles for the joint locker, which is discussed in more detail below. The external constraint 601 is configured to hold the end effector 222 in a predetermined position in the cavity 607 that corresponds to the homing position of the tool driver 230 or actuator 238. The external constraint 601 is secured onto the end effector by one or more fastening devices such as fasteners 603 (e.g., screws, bolts, etc.) through holes in the external constraint 601. The actuator 238 is driven to pull one or more corresponding cables. When the cable reaches a predetermined tension (e.g., 10 N or another value), the position of the actuator 238 or corresponding motor is measured, which may be referred to as the measured position or actual position of the motor. The controller 210 determines whether there is any deviation between the homing position and the measured position and calculates the difference between the homing position and the measured position. The difference between the homing position and the measured position is a calibration value. The controller may store the calibration value in memory associated with the corresponding identifier for the motor.

For the camera technique, the user may move the end effector 222 into the predetermined position manually (e.g., using a guide) by operating a joystick, touch control, wearable device, or other user input device. The guide may be a camera that aids in movement of the position of the end effector 222. In another embodiment of the camera technique, camera images of the end effector 222 are analyzed to determine the position of the end effector 222. From the analyzed images, motor commands are generated to move the end effector to the predetermined position.

For either the physical constraint technique or the camera technique, the positions (e.g., absolute position) of the corresponding actuator 238 and/or motor are measured, for example, by an encoder. For example, an encoder may convert the position or rotation of a shaft corresponding to the motor to an electrical signal. An absolute position encoder may provide a unique signal or output code for every position of rotation. In one example, the encoder includes a disk with a series of light and dark regions in a pattern that indicates position. Depending on the resolution of the encoder, a set number of concentric tracks are printed on the disk. The set number is the number of bits in the resolution of the encoder. As the tracks are simultaneously read by a sensor (e.g., optical sensor 347), a code having a bit for each track is determined. The code indicates the absolute position of the disk and corresponding actuator 238 and/or motor.

One or more calibration values may be determined based on the predetermined position of the end effector 222 and the measured position of the actuator 238 and/or motor. The calibration values may be a difference between the expected position of the actuator 238 and/or motor and the actual measured position of the actuator 238 and/or motor. The calibration may be a number of degrees or radians that the measured position deviates from the expected position.

The calibration values may include multiple values for different motors. The calibration values may be stored in a calibration file or calibration array. The calibration values may correspond to only the motors associated with cables. Referring to FIG. 6, this may include TD1-4. The calibration values may correspond to all of the motors, including one or more motors that are not associated with a cable. Referring to FIG. 6, this may include TD1-5 with TD5 associated with a gear train for the roll axis and not associated with a cable. In this example, the calibration file may include five tool motor positions corresponding to the wrist/roll home position, and also roll backlash.

The calibration values provide the motor position offset needed by (inverse) kinematic calculation. With an accurate calibration result, the control unit 210 determines an accurate map between motor position and wrist/roll position. Other unmodeled system factors such as compliance and friction may not be considered in this relationship.

At act S105, an evaluation of calibration is performed, for example, by the evaluation calibration algorithm or instructions 320 stored in memory 314 and executed by control unit 210. The following evaluation of calibration is an improvement over alternative calibration repeatability tests that are repeated multiple times on one instrument and compared across the calibration results generated from these processes. The comparison indicates pass criteria when there is small variation between different calibration results. However, this test result will only show how repeatable the calibration process is. This test result cannot answer whether the calibration result is accurate or not. It is possible that a bad calibration process can generate consistently wrong results. The following evaluation of calibration improves on this process because the calibration procedure itself is evaluated rather than merely the repeatability of the results.

For the evaluation procedure measurements are taken at multiple angular positions of the wrist that are not the zero position. The evaluation procedure measurements may span a region near the home position. In other words, the kinematic map for motor position and wrist/roll position pairs within a small region near the wrist/roll home position is evaluation.

Multiple sample points, including the motor position measured by a sensor (e.g., encoder) and wrist/roll position set by the physical constraint are compared. The region may be defined in a variety of techniques. The region may be defined according to an angle span and a constraint increment. The region may be centered at the zero position or the region may be centered at an offset from the zero position.

The sample points are the points spaced from the home position by the constraint increment and still with the angle span. For example, when the home position is at 0°, the constraint increment is 5°, and the angle span extends from −10° to +10°, then the sample points include −10°, −5°, +5°, and +10°. In some examples, 0° may also be a sample point but may be duplicative given that the physical constraint for calibration may depend on the same sample point.

The region may be defined by a user, for example, the user may enter values for the angle span, the constraint increment, and/or the offset, which are received by the control unit 210. In another example, the control unit 210 accesses memory 314 for the angle span, the constraint increment, and/or the offset.

In either case, the angle span, the constraint increment, and/or the offset define the shapes of the physical constraints. For each angle within the angle span at the constraint increment, a different physical constraint is used to take measurements.

Figure 11A:
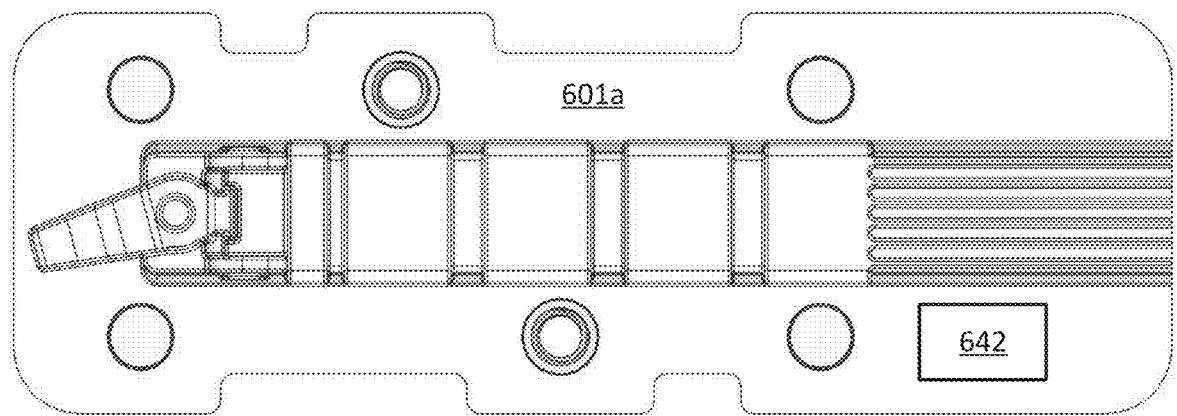
FIG. 11A illustrates an external constraint for a first angle.
Figure 11B:
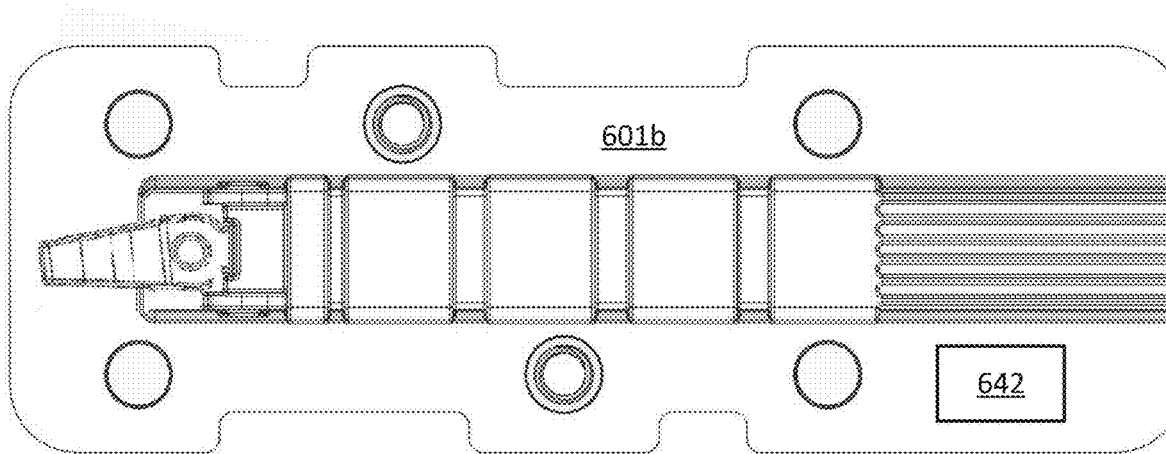
FIG. 11B illustrates an external constraint for a second angle.

FIG. 11 illustrates example physical constraints 601a and 601b for different sample point measurements in the calibration evaluation. Constraint 601a may be set for 15 degrees yaw angle, and constraint 601b may be set for 5 degrees yaw angle. Each physical constraint 601a-c includes at least one rigid member that contacts and holds the end effector 222 in a predetermined position. The physical constraints 601a-b may be a wrist locker including at least one rigid bracing member to hold the end effector 222.

The constraints may be numbered or otherwise identified with a constraint identifier. The user may place the constraint on the end effector and enter the constraint identifier to input device 317.

Alternatively, the physical constraint 601 and/or the constraint identifier may be automatically detected. For example, a sensor 643 may be present on the end effector 222 or the cannula 214 to detect the presence of the physical constraint 601. Alternatively, a sensor may be present at the surgical tool 240 to wireless detect the physical constraint.

In some examples only the presence of the physical constraint 601 is detected. For example, the end effector 222 may include a button or dip switch that is depressed when the physical constraint 601 is secured around the end effector 222. Alternatively, an optical sensor may detect the presence of the physical constraint 601 in proximity to the end effector 222.

In addition or in the alternative, the constraint identifier may be detected from the physical constraint 601. The control unit 210 may detect the constraint identifier from an identifier storage unit 642, such as a solid state memory, radio frequency identification (RFID) tag, bar code (including two-dimensional or matrix barcodes), etc., that identifies the physical constraint 601, an angle for the wrist position maintained by the physical constraint 601, or a set of angles for the wrist position such as first jaw angle, second jaw angle, roll angle and yaw angle.

The end effector 222 may include, for the sensor 632, a communication interface (e.g., a memory writer, a near field communications, near field communication (NFC), transceiver, RFID scanner, barcode reader, etc.) to read the information from the information storage unit 642 and pass the information to control unit 210.

Table 1 lists a set of measurements for the calibration evaluation. Each row in Table 1 corresponds to a different physical constraint being coupled to the end effector 222.

TABLE 1

| Constraint | Wrist Position | Tool Motor Position | Calculated Wrist Position |
|---|---|---|---|
| 1 | $Y_1$ | $X_1$ | $Y'_1$ |
| 2 | $Y_2$ | $X_2$ | $Y'_2$ |
| 3 | $Y_3$ | $X_3$ | $Y'_3$ |
| 4 | $Y_4$ | $X_4$ | $Y'_4$ |
| 5 | $Y_5$ | $X_5$ | $Y'_5$ |
| N | $Y_N$ | $X_N$ | $Y'_N$ |

Each wrist position Y and calculated wrist position Y' may comprise a set of angles. In one example, the set of angles $[\theta_1, \theta_2, \theta_3]$ includes the angle ($\theta_1$) between axis 452 and the axis 453 for the rotation angle around axis 420, angle ($\theta_2$) for the angle between jaw 401A and the axis 452, and angle ($\theta_3$) for the angle between jaw 401B and the axis 452. In another example, the set of angles $[\theta_{pitch}, \theta_{yaw}, \theta_{jaw}]$ includes pitch angle ($\theta_{pitch}$) of the end effector 222, the jaw angle ($\theta_{jaw}$) as the angle between the two jaws 401A and 401B, and the yaw angle ($\theta_{yaw}$) as the angle between the axis 452 and the line bisecting the jaw angle.

Equation 10 provides a calculation for the evaluation of calibration. A difference between the calculated wrist positions ($Y'_N$) and locked wrist positions ($Y_N$) is determined. This quantity is squared and the process repeats for each set of values (e.g., each physical constraint 601). Equation 10 is an example of a mean squared error (MSE) calculation. The angles y and y' may be Euler angles in 3D space. The difference between two Euler angles may be calculated using quaternions or rotation matrices.

$$1/N \, \Sigma_{i=1}^{n}(y_i - y'_i)^2 \qquad \text{Eq. 10}$$

The MSE calculation may be used to evaluate the absolute accuracy of calibration. For example, the result of the MSE calculation may be compared to a threshold (e.g., 2°, 5° or another number of degrees or radians).

Alternatively, there may be multiple tool motor positions measured for each physical constraint 601. For example, each of the motors that correspond to a cable may be measured for each physical constraint 601. Table 2 presents an example in which four motors drive cables for the jaws 401. Thus, for each constraint, a measurement is taken for each of the four tool disks (TD1, TD2, TD3, TD4).

TABLE 2

| Constraint | Tool Disk | Wrist Position | Tool Motor Position | Calculated Wrist Position |
|---|---|---|---|---|
| 1 | TD1 | $Y_{1,1}$ | $X_{1,1}$ | $Y'_{1,1}$ |
| 1 | TD2 | $Y_{1,2}$ | $X_{1,2}$ | $Y'_{1,2}$ |
| 1 | TD3 | $Y_{1,3}$ | $X_{1,3}$ | $Y'_{1,3}$ |
| 1 | TD4 | $Y_{1,4}$ | $X_{1,4}$ | $Y'_{1,4}$ |
| 2 | TD1 | $Y_{2,1}$ | $X_{2,1}$ | $Y'_{2,1}$ |
| 2 | TD2 | $Y_{2,2}$ | $X_{2,2}$ | $Y'_{2,2}$ |
| 2 | TD3 | $Y_{2,3}$ | $X_{2,3}$ | $Y'_{2,3}$ |
| 2 | TD4 | $Y_{2,4}$ | $X_{2,4}$ | $Y'_{2,4}$ |
| 3 | TD1 | $Y_{3,1}$ | $X_{3,1}$ | $Y'_{3,1}$ |
| 3 | TD2 | $Y_{3,2}$ | $X_{3,2}$ | $Y'_{3,2}$ |
| 3 | TD3 | $Y_{3,3}$ | $X_{3,3}$ | $Y'_{3,3}$ |
| 3 | TD4 | $Y_{3,4}$ | $X_{3,4}$ | $Y'_{3,4}$ |
| 4 | TD1 | $Y_{4,1}$ | $X_{4,1}$ | $Y'_{4,1}$ |
| 4 | TD2 | $Y_{4,2}$ | $X_{4,2}$ | $Y'_{4,2}$ |
| 4 | TD3 | $Y_{4,3}$ | $X_{4,3}$ | $Y'_{4,3}$ |
| 4 | TD4 | $Y_{4,4}$ | $X_{4,4}$ | $Y'_{4,4}$ |
| 5 | TD1 | $Y_{5,1}$ | $X_{5,1}$ | $Y'_{5,1}$ |
| 5 | TD2 | $Y_{5,2}$ | $X_{5,2}$ | $Y'_{5,2}$ |
| 5 | TD3 | $Y_{5,3}$ | $X_{5,3}$ | $Y'_{5,3}$ |
| 5 | TD4 | $Y_{5,4}$ | $X_{5,4}$ | $Y'_{5,4}$ |

Equation 11 provides another calculation of MSE for the evaluation of calibration across multiple actuators. A difference between the calculated wrist positions ($Y'_N$) and locked wrist positions ($Y_N$) is determined. This quantity is squared and the process repeats for each of the tool disks (summation over TD1 to TD4) and then repeats for each physical constraint 601 (summation over 1 to N).

$$1/(4N) \Sigma_{i=1}^{n} \Sigma_{TD=1}^{4} (y_i - y'_i)^2 \qquad \text{Eq. 11}$$

At act S107, feedback is provided based on the evaluation of calibration. The feedback may include a report that includes the results of the MSE calculation. The report may just include whether the calibration evaluation passed (the MSE result was less than the threshold) or failed (the MSE result was greater than the threshold). The feedback may be sent to the user in a message. For example, the message may be displayed at the display unit 319 for the tool driver 230. The control unit 210 may record a log in memory 314 including a timestamp for the feedback. The log may include multiple sets of data for the calibration evaluation taken over time (e.g., at a predetermined interval such as every hour, every day or in response to an event such as when the device is powered on). The user may also initiate the calibration evaluation and generation of the report via input device 317. The communication interface 318 may send the report to a central location (e.g., manufacturer device) or to a specified person via email, phone, or text.

At act S106, homing is performed in response to passing the calibration evaluation. Thus, homing may occur after calibration and after a successful evaluation calibration in which the MSE result is less than the threshold. The homing procedure may be performed in direction response to the calibration evaluation meeting the threshold. The homing process may bring the tool from the post-engagement configuration, which has a random nature, to a predetermined orientation. In response to successful homing, the tool control performs normal operation the process for one or more of the actuators of tool driver 230 to impart motion of their respective drive disks under the direction of commands from the user cause the motor to operate at a specific amount of torque, the drive disk to rotate to a specific location adjusted by the calibration values, as approved by the calibration evaluation. Through the homing process, a home position or a zero position for the actuator 238 of the tool driver 230 is established, which takes into account the calibration.

At act S108, the surgical tool 240 is ready to receive motor commands. For example, the user may enter position commands for the wrist. For example, the position commands for the wrist may be entered by joystick, touch control, wearable device, or directly to the tool driver by input device 317. Using Equation 4 above, the coordinate frame may be converted. Using the B matrix and the relationship of Equation 5 above, the cable displacements are determined. Using the linear relationship between cable displacements and the results of calibration and homing, the actuator displacements are calculated. The motor command is generated by the control unit 210 to move the appropriate actuator(s) 238 based on the actuator displacements.

Figure 12:
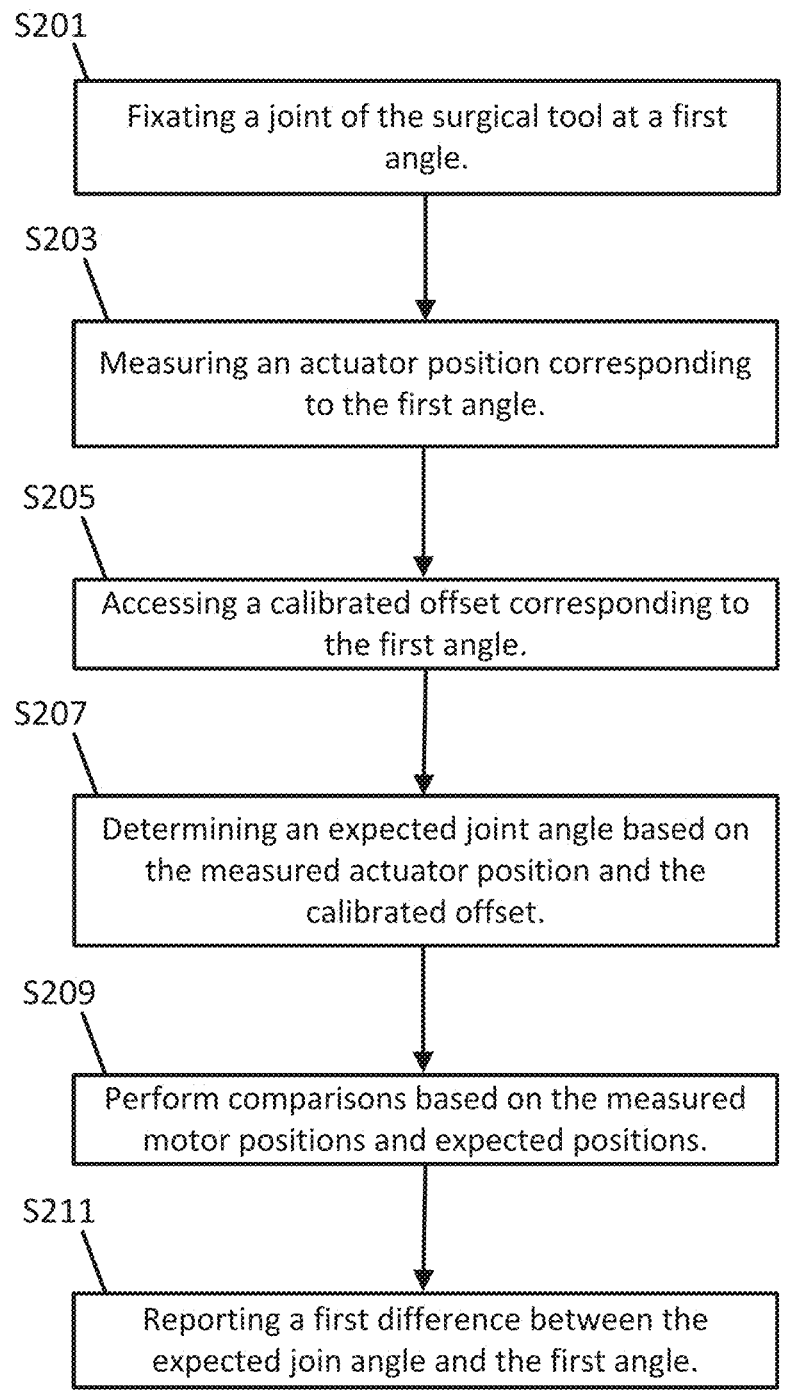
FIG. 12 illustrates a flow chart for an embodiment of the calibration evaluation procedure.

FIG. 12 describes a process for calibration evaluation. The process may be performed by a programmed processor (also referred to here as processor or controller), configured according to instructions stored in memory (e.g., the processor 312 and the memory 314 of FIG. 3, where the processor 312 is configured according to the instructions of the calibration control 316 and the calibration evaluation 315). Additional, different, or fewer acts than those in FIG. 12 may be performed.

At act S201, the process for calibration evaluation includes fixating a joint of the surgical tool at a first angle. The joint is driven by at least one actuator. Fixating the joint may include securing or coupling the joint, the end effector, or the robotic arm to a joint lock that sets the joint to an angle by including at least one rigid member that couples to the joint.

Optionally, the processor 312, in response to or before fixating the joint, identifies a lock identifier for a lock associated with at least one joint of the surgical tool. The lock identifier may be read from the lock itself (e.g., physical constraint 601) or be entered by the user at user input 317 or received from another device such as a network connection or wireless connection).

In some examples, the processor 312 provides motor commands in response to fixating the joint or the identification of the lock identifier. For example, the motor commands may drive the actuator 238 to achieve a predetermined tensioning force on the one or more cables before measuring the actuator position. In one example, the motor is moved in a predetermined direction while a torque is measured (e.g., by torque sensor 342) on the motor or associated cable to a predetermined torque. Different motor commands may be provided to different motors. In one example, four motors are associated with four cables and each motor is driven until an associated cable reaches the predetermined torque.

At act S203, the calibration evaluation process includes measuring an actuator position corresponding to the first angle. For example, the processor 312 determines a measured motor position for the motor. The sensor array 236 may detect the measured motor position in response to the predetermined tension being reached in the associated cable. The motor position may be determined by an encoder described herein, which may include the position sensor 343 and/or the optical sensor 347. In the example, with four motors, a different motor position may be determined for each motor. The processor 312 optionally stores, in memory 314, the determined motor positions in association with the lock identifier.

At act S205, the processor 312 accesses, from the memory 314, data for a calibrated offset corresponding to the first angle. The calibrated offset may be accessed from a calibration profile stored in a memory of the surgical tool. The calibration profile includes a plurality of offsets for compensating actuator backlash at a plurality of joint angles centered at zero degree.

At act S207, the processor 312 determines an expected joint angle based on the measured actuator position and the calibrated offset. The processor 312 applies the calibrated offset to the measured actuator position to produce an offset actuator position corresponding to the first angle. The processor 312 may convert the offset actuator position to the expected joint angle based on a kinematic model of the joint. In some examples, the measured motor positions are converted through the relationships described herein to the corresponding wrist position or position of the end effector 222. Thus, in these examples, the expected positions are expected wrist or end effector positions. In other examples, the expected positions are expected motor positions. For example, the memory 314 may include a table that associates lock identifiers with motor positions. The processor 312 may sort the expected motor positions and the corresponding measured motor positions into a table.

The processor 312 may calculate an evaluation value from the combination of results of the comparisons based on the measured motor positions and the expected positions (either expected motor positions or expected end effector positions). The processor may generate a table for the measured positions (either measured motor positions or calculated end effector positions) and expected positions (either expected motor positions or expected end effector positions) for a particular motor across all of the wrist lockers. The processor 312 may calculate differences between the measured positions to the expected positions for the first locker, the second locker, and any subsequent lockers. The differences are summed as the evaluation value. In another example, the difference values are averaged as the evaluation value. In another example, the difference values are squared then summed as the evaluation value. Thus, the processor 312 calculates an evaluation value for each actuator or motor that spans all of the wrist lockers used.

As an alternative or in addition, the processor may calculate an evaluation value specific to a single wrist locker. The processor 312 may perform one or more operations on the table that includes the expected motor positions and the corresponding measured motor positions. The processor 312 may subject the expected positions and the corresponding measured positions and perform the absolute value thereof. The result of subtraction (difference values) may be summed as the evaluation value. In another example, the difference values are averaged as the evaluation value. In another example, the difference values are squared then summed as the evaluation value.

At act S211, the processor 312 reports a first difference between the expected join angle and the first angle. As described in more detail in earlier embodiments, the processor 312 may generate a message or other combination that indicates the evaluation value or compares the evaluation value to one or more thresholds to conclude whether a particular motor or the tool as a whole passed the calibration evaluation test. The processor 312 may calculate a mean squared error based on a comparison of the evaluation value of a threshold.

These acts (S201, S203, S205, S207, S209, and S211) may be repeated for multiple lockers. The joint may be fixated at a second angle using a second joint lock. The processor 312 acquires a second actuator position and a second calibrated offset corresponding to the second angle. The processor 312 determines a second expected joint angle based on the second actuator position and the second calibrated offset. The processor 312 calculates a second difference between the second expected join angle and the second angle.

Herein, the phrase "coupled with" is defined to mean directly connected to or indirectly connected through one or more intermediate components. Such intermediate components may include both hardware- and software-based components. Further, to clarify the use in the pending claims and to hereby provide notice to the public, the phrases "at least one of <A>, <B>, . . . and <N>" or "at least one of <A>, <B>, . . . <N>, or combinations thereof" are defined by the Applicant in the broadest sense, superseding any other implied definitions hereinbefore or hereinafter unless expressly asserted by the Applicant to the contrary, to mean one or more elements selected from the group comprising A, B, . . . and N, that is to say, any combination of one or more of the elements A, B, . . . or N including any one element alone or in combination with one or more of the other elements which may also include, in combination, additional elements not listed.

The disclosed mechanisms may be implemented at any logical and/or physical point(s), or combinations thereof, at which the relevant information/data (e.g., message traffic and responses thereto) may be monitored or flows or is otherwise accessible or measurable, including one or more gateway devices, modems, computers or terminals of one or more market participants, e.g., client computers, etc.

One skilled in the art will appreciate that one or more modules described herein may be implemented using, among other things, a tangible computer-readable medium comprising computer-executable instructions (e.g., executable software code). Alternatively, modules may be implemented as software code, firmware code, specifically configured hardware or processors, and/or a combination of the aforementioned.

The operations of computer devices and systems shown in FIGS. 1-25 may be controlled by computer-executable instructions stored on a non-transitory computer-readable medium. For example, the exemplary computer device or control unit 210 may store computer-executable instructions, generate electronic messages, extracting information from the electronic messages, executing actions relating to the electronic messages, and/or calculating values from the electronic messages to facilitate any of the algorithms or acts described herein. Numerous additional servers, computers, handheld devices, personal digital assistants, telephones and other devices may also be connected to control unit 210.

As illustrated in FIG. 3, the computer system may include a processor 312 implemented by a central processing unit (CPU), a graphics processing unit (GPU), or both. The processor 312 may be a component in a variety of systems. For example, the processor 312 may be part of a standard personal computer or a workstation. The processor 312 may be one or more general processors, digital signal processors, specifically configured processors, application specific integrated circuits, field programmable gate arrays, servers, networks, digital circuits, analog circuits, combinations thereof, or other now known or later developed devices for analyzing and processing data. The processor 312 may implement a software program, such as code generated manually (i.e., programmed).

The computer system includes memory 314 that can communicate via a bus. The memory 314 may be a main memory, a static memory, or a dynamic memory. The memory 314 may include, but is not limited to, computer-readable storage media such as various types of volatile and non-volatile storage media, including but not limited to random-access memory, read-only memory, programmable read-only memory, electrically programmable read-only memory, electrically erasable read-only memory, flash memory, magnetic tape or disk, optical media and the like. In one embodiment, the memory 314 includes a cache or random-access memory for the processor 312. In alternative embodiments, the memory 314 is separate from the processor 312, such as a cache memory of a processor, the system memory, or other memory. The memory 314 may be an external storage device or database for storing data. Examples include a hard drive, compact disk ("CD"), digital video disc ("DVD"), memory card, memory stick, floppy disk, universal serial bus ("USB") memory device, or any other device operative to store data. The memory 314 is operable to store instructions executable by the processor 312. The functions, acts or tasks illustrated in the figures or described herein may be performed by the programmed processor 312 executing the instructions stored in the memory 314. The functions, acts or tasks are independent of the particular type of instructions set, storage media, processor or processing strategy and may be performed by software, hardware, integrated circuits, firmware, micro-code and the like, operating alone or in combination. Likewise, processing strategies may include multiprocessing, multitasking, parallel processing and the like.

The computer system may further include a display unit 319, such as a liquid crystal display (LCD), an organic light emitting diode (OLED), a flat panel display, a solid-state display, a cathode ray tube (CRT), a projector, a printer or other now known or later developed display device for outputting determined information. The display 319 may act as an interface for the user to see the functioning of the processor 312, or specifically as an interface with the instructions stored in the memory 314 or elsewhere in the control unit 210.

Additionally, the computer system may include an input device 317 configured to allow a user to interact with any of the components of the system. The input device 317 may be a number pad, a keyboard, or a cursor control device, such as a mouse, or a joystick, touch screen display, remote control or any other device operative to interact with the control unit 210.

The present disclosure contemplates a computer-readable medium that includes instructions or receives and executes instructions responsive to a signal, so that a device connected to a network can communicate voice, video, audio, images or any other data over the network. Further, the instructions may be transmitted or received over the network via a communication interface 318. The communication interface 318 may be a part of the processor 312 or may be a separate component. The communication interface 218 may be a physical connection in hardware. The communication interface 318 is configured to connect with a network, external media, the display unit 319, or any other components in the system, or combinations thereof. The connection with the network may be a physical connection, such as a wired Ethernet connection or may be established wirelessly. Likewise, the additional connections with other components of the system may be physical connections or may be established wirelessly.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the described embodiments should not be understood as requiring such separation in all embodiments, and it should be understood that the described program components and systems can generally be integrated together in a single software product or packaged into multiple software products.

What is claimed is:

1. A computer-implemented method for evaluating calibrations of a surgical tool, the method comprising:
   fixating a joint of the surgical tool at a first angle, the joint being driven by an actuator;
   measuring an actuator position corresponding to the first angle;
   accessing a calibrated offset corresponding to the first angle;
   determining an expected joint angle based on the measured actuator position and the calibrated offset; and
   reporting a first difference between the expected joint angle and the first angle.

2. The method of claim 1, wherein the joint includes a roll joint, a wrist joint, or one or more jaw joints of the surgical tool.

3. The method of claim 1, wherein the joint is driven by the actuator through one or more cables.

4. The method of claim 3, further comprising:
driving the actuator to achieve a predetermined tensioning force on the one or more cables before measuring the actuator position.

5. The method of claim 1, wherein the joint is fixated at an angle by a joint lock including at least one rigid member that couples to the joint.

6. The method of claim 1, wherein the calibrated offset is accessed from a calibration profile stored in a memory of the surgical tool, and
wherein the calibration profile includes a plurality of offsets for compensating actuator backlash at a plurality of joint angles centered at zero degree.

7. The method of claim 1, wherein determining the expected joint angle comprises:
applying the calibrated offset to the measured actuator position to produce an offset actuator position corresponding to the first angle; and
converting the offset actuator position to the expected joint angle based on a kinematic model of the joint.

8. The method of claim 1, further comprising:
fixating the joint at a second angle;
acquiring a second actuator position and a second calibrated offset corresponding to the second angle;
determining a second expected joint angle based on the second actuator position and the second calibrated offset; and
calculating a second difference between the second expected joint angle and the second angle.

9. The method of claim 8, further comprising:
calculating a mean squared error based on at least the first difference and the second difference.

10. The method of claim 9, further comprising:
reporting an inaccurate calibration if the calculated mean squared error exceeds a predetermined threshold.

11. A system for calibration of a surgical tool, the system comprising:
a surgical tool connected to and driven by at least one actuator; and
one or more processors configured to:
measure an actuator position corresponding to a joint of the surgical tool fixated at a first angle, the joint being driven by the actuator;
access a calibrated offset corresponding to the first angle;
determine an expected joint angle based on the measured actuator position and the calibrated offset; and
report a first difference between the expected joint angle and the first angle.

12. The system of claim 11, wherein the joint includes a roll joint, a wrist joint, or one or more jaw joints of the surgical tool.

13. The system of claim 11, wherein the joint is driven by the actuator through one or more cables.

14. The system of claim 11, wherein the joint is fixated at an angle by a joint lock including at least one rigid member that couples to the joint.

15. The system of claim 11, wherein the calibrated offset is accessed from a calibration profile stored in a memory of the surgical tool, and
wherein the calibration profile includes a plurality of offsets for compensating actuator backlash at a plurality of joint angles centered at zero degree.

16. The system of claim 11, wherein the one or more processors are configured to:
apply the calibrated offset to the measured actuator position to produce an offset actuator position corresponding to the first angle; and
convert the offset actuator position to the expected joint angle based on a kinematic model of the joint.

17. The system of claim 11, wherein the one or more processors are configured to:
acquire a second actuator position and a second calibrated offset corresponding to a second angle;
determine a second expected joint angle based on the second actuator position and the second calibrated offset; and
calculate a second difference between the second expected joint angle and the second angle.

18. The system of claim 17, wherein the one or more processors are configured to:
calculate a mean squared error based on at least the first difference and the second difference.

19. The system of claim 18, wherein the one or more processors are configured to:
report an inaccurate calibration if the calculated mean squared error exceeds a predetermined threshold.

20. An apparatus for evaluation of a surgical tool, the apparatus comprising:
a memory storing expected values for a plurality of motors coupled to the surgical tool;
one or more processors further configured to:
identify at least one lock identifier for a lock associated with at least one joint of the surgical tool;
determine a position associated with at least one of the plurality of motors and the at least one lock identifier;
access data for an expected position from the memory; and
perform a comparison of the determined position to the expected position.

* * * * *